(12) United States Patent
Nyahay et al.

(10) Patent No.: US 12,279,968 B2
(45) Date of Patent: *Apr. 22, 2025

(54) IMPLANT WITH BONE CONTACTING ELEMENTS HAVING HELICAL AND UNDULATING PLANAR GEOMETRIES

(71) Applicant: Institute for Musculoskeletal Science and Education, Ltd., King of Prussia, PA (US)

(72) Inventors: Joseph M. Nyahay, Eagleville, PA (US); Edward J. McShane, III, Collegeville, PA (US); Sean S. Bishop, Malvern, PA (US); Christopher J. Ryan, Lincoln University, PA (US); Megan A. Stauffer, Wayne, PA (US)

(73) Assignee: Institute for Musculoskeletal Science and Education, Ltd., King of Prussia, PA (US)

( * ) Notice: Subject to any disclaimer, the term of this patent is extended or adjusted under 35 U.S.C. 154(b) by 590 days.

This patent is subject to a terminal disclaimer.

(21) Appl. No.: 17/515,836

(22) Filed: Nov. 1, 2021

(65) Prior Publication Data

US 2022/0047398 A1 Feb. 17, 2022

Related U.S. Application Data

(63) Continuation of application No. 16/449,839, filed on Jun. 24, 2019, now Pat. No. 11,160,668, which is a
(Continued)

(51) Int. Cl.
*A61F 2/44* (2006.01)
*A61F 2/46* (2006.01)
*A61F 2/30* (2006.01)

(52) U.S. Cl.
CPC ............ *A61F 2/447* (2013.01); *A61F 2/4455* (2013.01); *A61F 2/4611* (2013.01);
(Continued)

(58) Field of Classification Search
CPC ...... A61F 2/447; A61F 2/4455; A61F 2/4611; A61F 2002/30112; A61F 2002/30136;
(Continued)

(56) References Cited

U.S. PATENT DOCUMENTS

| | | |
|---|---|---|
| 4,917,704 A | 4/1990 | Frey et al. |
| 4,961,740 A | 10/1990 | Ray et al. |

(Continued)

FOREIGN PATENT DOCUMENTS

| | | |
|---|---|---|
| JP | 2013535264 | 7/2011 |
| JP | 2013500772 | 1/2013 |

(Continued)

OTHER PUBLICATIONS

International Search Report and Written Opinion for PCT application PCT/US2016/029865 mailed Aug. 19, 2016.

(Continued)

*Primary Examiner* — Tessa M Matthews
*Assistant Examiner* — David C Comstock
(74) *Attorney, Agent, or Firm* — Plumsea Law Group, LLC

(57) ABSTRACT

An implant may include a first body member and a second body member, at least one bone contacting arched member, and a first external element extending from the first body member to the second body member, wherein the first external element has an undulating planar geometry in which the first external element undulates in a single plane.

20 Claims, 34 Drawing Sheets

Related U.S. Application Data continuation of application No. 15/457,515, filed on Mar. 13, 2017, now Pat. No. 10,357,377.

(52) U.S. Cl.
CPC ............... *A61F 2002/30112* (2013.01); *A61F 2002/30136* (2013.01); *A61F 2002/30153* (2013.01); *A61F 2002/30289* (2013.01); *A61F 2002/30291* (2013.01); *A61F 2002/3092* (2013.01); *A61F 2002/3093* (2013.01); *A61F 2002/4495* (2013.01); *A61F 2002/4629* (2013.01)

(58) Field of Classification Search
CPC .. A61F 2002/30153; A61F 2002/30289; A61F 2002/30291; A61F 2002/3092; A61F 2002/3093; A61F 2002/4495; A61F 2002/4629
USPC ........................................... 623/17.11, 17.16
See application file for complete search history.

(56) References Cited

U.S. PATENT DOCUMENTS

| | | |
|---|---|---|
| 5,423,816 A | 6/1995 | Lin |
| 5,458,638 A | 10/1995 | Kuslich et al. |
| 5,571,192 A | 11/1996 | Schonhoffer |
| 5,607,424 A | 3/1997 | Tropiano |
| 5,609,635 A | 3/1997 | Michelson |
| 5,658,337 A | 8/1997 | Kohrs et al. |
| 5,709,683 A | 1/1998 | Bagby |
| 5,716,416 A | 2/1998 | Lin |
| 5,897,556 A | 4/1999 | Drewry et al. |
| 6,039,762 A | 3/2000 | McKay |
| 6,090,143 A | 7/2000 | Meriwether et al. |
| 6,126,689 A | 10/2000 | Brett |
| 6,149,651 A | 11/2000 | Drewry et al. |
| 6,200,348 B1 | 3/2001 | Biedermann et al. |
| 6,206,924 B1 | 3/2001 | Timm |
| 6,241,770 B1 | 6/2001 | Michelson |
| 6,371,987 B1 | 4/2002 | Weiland et al. |
| 6,428,575 B2 | 8/2002 | Koo et al. |
| 6,436,141 B2 | 8/2002 | Castro et al. |
| 6,494,883 B1 | 12/2002 | Ferree |
| 6,500,205 B1 | 12/2002 | Michelson |
| 6,520,996 B1 | 2/2003 | Manasas et al. |
| 6,527,805 B2 | 3/2003 | Studer et al. |
| 6,537,320 B1 | 3/2003 | Michelson |
| 6,582,467 B1 | 6/2003 | Teitelbaum et al. |
| 6,585,770 B1 | 7/2003 | White et al. |
| 6,616,695 B1 | 9/2003 | Crozet et al. |
| 6,709,458 B2 | 3/2004 | Michelson |
| 6,758,849 B1 | 7/2004 | Michelson |
| 6,808,537 B2 | 10/2004 | Michelson |
| 6,846,327 B2 | 1/2005 | Khandkar et al. |
| 6,863,689 B2 | 3/2005 | Ralph et al. |
| 6,923,810 B1 | 8/2005 | Michelson |
| 6,962,606 B2 | 11/2005 | Michelson |
| 6,997,953 B2 | 2/2006 | Chung et al. |
| 7,141,068 B2 | 11/2006 | Ross et al. |
| 7,186,267 B2 | 3/2007 | Aston et al. |
| 7,341,601 B2 | 3/2008 | Eisermann et al. |
| 7,410,501 B2 | 8/2008 | Michelson |
| 7,429,270 B2 | 9/2008 | Baumgartner et al. |
| 7,435,261 B1 | 10/2008 | Castro |
| 7,452,369 B2 | 11/2008 | Barry |
| 7,485,134 B2 | 2/2009 | Simonson |
| 7,527,649 B1 | 5/2009 | Blain |
| 7,537,616 B1 | 5/2009 | Branch et al. |
| 7,621,952 B2 | 11/2009 | Truckai et al. |
| 7,621,953 B2 | 11/2009 | Braddock, Jr. et al. |
| 7,628,814 B2 | 12/2009 | Studer et al. |
| 7,794,500 B2 | 9/2010 | Felix |
| 7,799,056 B2 | 9/2010 | Sankaran |
| 7,803,191 B2 | 9/2010 | Biedermann et al. |
| 7,879,100 B2 | 2/2011 | Denoziere et al. |
| 7,879,103 B2 | 2/2011 | Gertzman |
| 7,935,149 B2 | 5/2011 | Michelson |
| 8,016,887 B1 | 9/2011 | Castro |
| 8,021,424 B2 | 9/2011 | Beger et al. |
| 8,021,426 B2 | 9/2011 | Segal et al. |
| 8,062,365 B2 | 11/2011 | Schwab |
| 8,092,536 B2 | 1/2012 | Ahrens et al. |
| 8,182,538 B2 | 5/2012 | O'Neil et al. |
| 8,226,718 B2 | 7/2012 | Castro |
| 8,241,363 B2 | 8/2012 | Sommerich et al. |
| 8,246,683 B2 | 8/2012 | Castro |
| 8,298,286 B2 | 10/2012 | Trieu |
| 8,328,848 B2 | 12/2012 | Lowery et al. |
| 8,361,149 B2 | 1/2013 | Castro |
| 8,414,820 B2 | 4/2013 | Bertele et al. |
| 8,430,930 B2 | 4/2013 | Hunt |
| 8,435,300 B2 | 5/2013 | Messerli et al. |
| 8,454,700 B2 | 6/2013 | Lemoine et al. |
| 8,475,533 B1 | 7/2013 | Castro |
| 8,551,173 B2 | 10/2013 | Lechmann et al. |
| 8,556,978 B2 | 10/2013 | Schaller |
| 8,613,769 B2 | 12/2013 | Sears et al. |
| 8,623,090 B2 | 1/2014 | Butler |
| 8,673,006 B2 | 3/2014 | Castro |
| 8,709,042 B2 | 4/2014 | Greenhalgh et al. |
| 8,740,981 B2 | 6/2014 | Tornier et al. |
| 8,771,357 B2 | 7/2014 | Biedermann et al. |
| 8,771,368 B2 | 7/2014 | McKay |
| 8,795,362 B2 | 8/2014 | Anderson et al. |
| 8,801,787 B2 | 8/2014 | Schaller |
| 8,808,376 B2 | 8/2014 | Schaller |
| 8,808,725 B2 | 8/2014 | Altschuler et al. |
| 8,932,356 B2 | 1/2015 | Kraus |
| 8,940,052 B2 | 1/2015 | Lechmann et al. |
| 8,951,300 B2 | 2/2015 | Parrish |
| 8,986,383 B2 | 3/2015 | Castro |
| 9,039,766 B1* | 5/2015 | Fonte .................... A61F 2/3094 623/17.13 |
| 9,173,746 B2 | 11/2015 | Lowery et al. |
| 9,186,252 B2 | 11/2015 | Leibinger |
| 9,186,257 B2 | 11/2015 | Geisler et al. |
| 9,247,970 B2 | 2/2016 | Teisen |
| 9,271,845 B2 | 3/2016 | Hunt et al. |
| 9,295,562 B2 | 3/2016 | Lechmann et al. |
| 9,402,733 B1 | 8/2016 | To et al. |
| 9,408,651 B2 | 8/2016 | Sennett et al. |
| 9,421,108 B2 | 8/2016 | Hunt |
| 9,770,339 B2 | 9/2017 | Greenhalgh |
| 9,918,849 B2 | 3/2018 | Morris et al. |
| 10,245,152 B2 | 4/2019 | Kloss |
| 10,357,377 B2 | 7/2019 | Nyahay et al. |
| 2001/0014826 A1 | 8/2001 | Biedermann et al. |
| 2001/0032018 A1 | 10/2001 | Castro et al. |
| 2002/0052656 A1 | 5/2002 | Michelson |
| 2002/0123750 A1 | 9/2002 | Eisermann et al. |
| 2003/0018389 A1 | 1/2003 | Castro |
| 2003/0078660 A1 | 4/2003 | Clifford et al. |
| 2003/0083746 A1 | 5/2003 | Kuslich |
| 2004/0082953 A1 | 4/2004 | Petit |
| 2004/0122518 A1* | 6/2004 | Rhoda .................... A61F 2/4611 623/17.11 |
| 2004/0193270 A1 | 9/2004 | DiMauro et al. |
| 2004/0210312 A1 | 10/2004 | Neumann |
| 2004/0225361 A1 | 11/2004 | Glenn et al. |
| 2005/0033294 A1* | 2/2005 | Garden ............... A61B 17/7059 606/247 |
| 2005/0177238 A1 | 8/2005 | Khandkar et al. |
| 2005/0222681 A1 | 10/2005 | Richley et al. |
| 2005/0278027 A1 | 12/2005 | Hyde, Jr. |
| 2005/0278028 A1 | 12/2005 | Mujwid |
| 2006/0041262 A1 | 2/2006 | Calvert et al. |
| 2006/0052872 A1 | 3/2006 | Studer et al. |
| 2006/0052873 A1 | 3/2006 | Buck et al. |
| 2006/0058881 A1 | 3/2006 | Trieu |
| 2006/0100706 A1 | 5/2006 | Shadduck et al. |
| 2006/0147332 A1 | 7/2006 | Jones et al. |

(56) References Cited

U.S. PATENT DOCUMENTS

| | | | |
|---|---|---|---|
| 2006/0241760 A1* | 10/2006 | Randall | A61F 2/447 623/17.11 |
| 2006/0247781 A1* | 11/2006 | Francis | A61F 2/442 606/78 |
| 2006/0293753 A1 | 12/2006 | Thramann | |
| 2007/0027544 A1 | 2/2007 | McCord et al. | |
| 2007/0050032 A1 | 3/2007 | Gittings et al. | |
| 2007/0179610 A1 | 8/2007 | Biedermann et al. | |
| 2007/0198090 A1 | 8/2007 | Abdou | |
| 2007/0219634 A1 | 9/2007 | Greenhalgh | |
| 2007/0260324 A1 | 11/2007 | Joshi et al. | |
| 2008/0077244 A1 | 3/2008 | Robinson | |
| 2008/0306595 A1 | 12/2008 | McLeod et al. | |
| 2008/0312742 A1 | 12/2008 | Abernathie | |
| 2009/0036985 A1 | 2/2009 | Whiting | |
| 2009/0048678 A1 | 2/2009 | Saal et al. | |
| 2009/0112321 A1 | 4/2009 | Kitchen | |
| 2009/0149958 A1 | 6/2009 | Prewett et al. | |
| 2009/0248162 A1 | 10/2009 | Peckham | |
| 2010/0137990 A1 | 6/2010 | Apatsidis et al. | |
| 2010/0191337 A1* | 7/2010 | Zamani | A61F 2/4465 623/17.16 |
| 2010/0286778 A1 | 11/2010 | Eisermann et al. | |
| 2010/0286783 A1 | 11/2010 | Lechmann | |
| 2011/0015741 A1 | 1/2011 | Melkent et al. | |
| 2011/0029083 A1 | 2/2011 | Hynes et al. | |
| 2011/0066192 A1 | 3/2011 | Frasier et al. | |
| 2011/0106261 A1 | 5/2011 | Chin et al. | |
| 2011/0130839 A1* | 6/2011 | Harms | A61F 2/442 623/17.16 |
| 2011/0166660 A1 | 7/2011 | Laurence | |
| 2011/0172775 A1 | 7/2011 | Flickinger et al. | |
| 2011/0190895 A1 | 8/2011 | Segal et al. | |
| 2011/0245926 A1 | 10/2011 | Kitchen | |
| 2011/0270401 A1 | 11/2011 | McKay | |
| 2011/0301709 A1 | 12/2011 | Kraus et al. | |
| 2011/0313532 A1 | 12/2011 | Hunt | |
| 2012/0191188 A1 | 7/2012 | Huang | |
| 2012/0191189 A1 | 7/2012 | Huang | |
| 2012/0203346 A1 | 8/2012 | Kraus | |
| 2012/0296431 A1 | 11/2012 | Kim et al. | |
| 2013/0030529 A1 | 1/2013 | Hunt | |
| 2013/0116793 A1 | 5/2013 | Kloss | |
| 2013/0123935 A1 | 5/2013 | Hunt et al. | |
| 2013/0158672 A1 | 6/2013 | Hunt | |
| 2013/0184826 A1 | 7/2013 | Thaiyananthan | |
| 2013/0190880 A1 | 7/2013 | Schaller | |
| 2013/0218282 A1 | 8/2013 | Hunt | |
| 2013/0218288 A1 | 8/2013 | Fonte et al. | |
| 2013/0304211 A1 | 11/2013 | Trautwein et al. | |
| 2013/0345812 A1 | 12/2013 | Errico et al. | |
| 2014/0058513 A1 | 2/2014 | Gahman et al. | |
| 2014/0121776 A1 | 5/2014 | Hunt | |
| 2014/0142707 A1 | 5/2014 | Compton et al. | |
| 2014/0195005 A1 | 7/2014 | McKay | |
| 2014/0243980 A1 | 8/2014 | Sack et al. | |
| 2014/0277457 A1 | 9/2014 | Yeung et al. | |
| 2014/0277464 A1 | 9/2014 | Richter et al. | |
| 2014/0277569 A1 | 9/2014 | Lange | |
| 2014/0288649 A1 | 9/2014 | Hunt | |
| 2014/0288650 A1 | 9/2014 | Hunt | |
| 2014/0303745 A1 | 10/2014 | Anderson et al. | |
| 2014/0309743 A1 | 10/2014 | Falahee | |
| 2014/0358246 A1 | 12/2014 | Levy et al. | |
| 2015/0100125 A1* | 4/2015 | Protopsaltis | A61F 2/4455 623/17.15 |
| 2015/0127106 A1 | 5/2015 | Partee et al. | |
| 2015/0282933 A1 | 10/2015 | Hunt | |
| 2015/0282945 A1 | 10/2015 | Hunt | |
| 2015/0282946 A1 | 10/2015 | Hunt | |
| 2016/0045230 A1 | 2/2016 | Lowery et al. | |
| 2016/0081809 A1 | 3/2016 | Schneider et al. | |
| 2016/0193057 A1 | 7/2016 | Rhoda | |
| 2016/0206439 A1 | 7/2016 | To et al. | |
| 2016/0206440 A1 | 7/2016 | DeRidder et al. | |
| 2016/0324656 A1 | 11/2016 | Morris et al. | |
| 2017/0042697 A1 | 2/2017 | McShane, III et al. | |
| 2017/0156879 A1* | 6/2017 | Janowski | A61F 2/4611 |
| 2017/0216034 A1 | 8/2017 | Daniel et al. | |
| 2018/0110626 A1 | 4/2018 | Mcshane, III et al. | |
| 2018/0140341 A1 | 5/2018 | Fischer Lokou | |
| 2018/0256353 A1 | 9/2018 | Nyahay et al. | |

FOREIGN PATENT DOCUMENTS

| | | | |
|---|---|---|---|
| WO | 2009-051779 A1 | | 4/2009 |
| WO | 2010-097632 A1 | | 9/2010 |
| WO | 2011-159587 A1 | | 12/2011 |
| WO | 2013-019543 A2 | | 2/2013 |
| WO | WO 2016181078 | | 11/2016 |

OTHER PUBLICATIONS

Office Action mailed May 5, 2017 in U.S. Appl. No. 15/141,655.
U.S. Appl. No. 15/334,022, filed Oct. 25, 2016.
Office Action mailed May 15, 2018 in U.S. Appl. No. 15/457,515.
Final Office Action mailed Nov. 29, 2018 in U.S. Appl. No. 15/457,515.
Office Action mailed Oct. 30, 2020 in U.S. Appl. No. 16/449,839.
International Search Report and Written Opinion mailed Aug. 9, 2018 in PCT/US2018/22021.
Office Action mailed Feb. 3, 2022 in JP Application No. 2019-550216.
Office Action mailed Sep. 1, 2022 in JP Application No. 2019-550216.
Office Action mailed Apr. 12, 2024 in U.S. Appl. No. 17/515,836.
Final Office Action mailed Sep. 4, 2024 in U.S. Appl. No. 17/515,836.

* cited by examiner

IMPLANT WITH BONE CONTACTING ELEMENTS HAVING HELICAL AND UNDULATING PLANAR GEOMETRIES

CROSS-REFERENCE TO RELATED APPLICATIONS

This application is a continuation of Nyahay et al., U.S. Publication No. 2019/0307574, published on Oct. 10, 2019, and entitled "Implant with Bone Contacting Elements Having Helical and Undulating Planar Geometries," which is a continuation of Nyahay et al., U.S. Publication No. 2018/0256352, published on Sep. 13, 2018, and entitled "Implant with Bone Contacting Elements Having Helical and Undulating Planar Geometries," the entire disclosures of which are incorporated herein by reference.

BACKGROUND

The embodiments are generally directed to implants for supporting bone growth in a patient.

A variety of different implants are used in the body. Implants used in the body to stabilize an area and promote bone ingrowth provide both stability (i.e. minimal deformation under pressure over time) and space for bone ingrowth.

Spinal fusion, also known as spondylodesis or spondylosyndesis, is a surgical treatment method used for the treatment of various morbidities such as degenerative disc disease, spondylolisthesis (slippage of a vertebra), spinal stenosis, scoliosis, fracture, infection or tumor. The aim of the spinal fusion procedure is to reduce instability and thus pain.

In preparation for the spinal fusion, most of the intervertebral disc is removed. An implant, the spinal fusion cage, may be placed between the vertebra to maintain spine alignment and disc height. The fusion, i.e. bone bridge, occurs between the endplates of the vertebrae.

SUMMARY

In one aspect, an implant includes a first body member and a second body member, a first bone contacting element having a first sidewall and a second bone contacting element having a second sidewall. The first bone contacting element extends from the first body member to the second body member and the second bone contacting element extends from the first body member to the second body member. The first sidewall of the first bone contacting element is attached to the second sidewall of the second bone contacting element at a connecting portion.

In another aspect, an implant includes a first body member, a second body member and a bone contacting element extending from the first body member to the second body member. The bone contacting element has an undulating planar geometry.

In another aspect, an implant includes a superior side, an inferior side and a lateral side. The implant also includes a first body member and a second body member. The implant also includes a first bone contacting element extending from the first body member to the second body member, where the first bone contacting element is disposed adjacent a location where the lateral side meets the superior side. The implant also includes a second bone contacting element extending from the first body member to the second body member, where the second bone contacting element is disposed adjacent a location where the lateral side meets the inferior side. The implant also includes a support wall extending on the lateral side between the first bone contacting element and the second bone contacting element. The implant also includes a third bone contacting element intersecting the support wall.

In another aspect, an implant includes a first body member and a second body member. The implant also includes a first direction extending from the first body member to the second body member and a second direction perpendicular to the first direction. The implant also includes a central bone contacting element generally extending along the second direction. The central bone contacting element has an undulating planar geometry.

Other systems, methods, features and advantages of the embodiments will be, or will become, apparent to one of ordinary skill in the art upon examination of the following figures and detailed description. It is intended that all such additional systems, methods, features and advantages be included within this description and this summary, be within the scope of the embodiments, and be protected by the following claims.

BRIEF DESCRIPTION OF THE DRAWINGS

The embodiments can be better understood with reference to the following drawings and description. The components in the figures are not necessarily to scale, emphasis instead being placed upon illustrating the principles of the embodiments. Moreover, in the figures, like reference numerals designate corresponding parts throughout the different views.

DETAILED DESCRIPTION

The embodiments described herein are directed to an implant for use in a spine. In addition to the various provisions discussed below, any embodiments may make use of any of the body/support structures, frames, plates, coils or other structures disclosed in Morris et al., U.S. Publication Number 2016/0324656, published on Nov. 10, 2016, currently U.S. patent application Ser. No. 15/141,655, filed on Apr. 28, 2016 and titled "Coiled Implants and Systems and Methods of Use Thereof," which is hereby incorporated by reference in its entirety. For purposes of convenience, the Morris application will be referred to throughout the present application as "The Coiled Implant Application". Also, any embodiments may make use of any of the body/support structures, members, elements, frames, plates or other structures disclosed in McShane III et al., U.S. Publication Number 2017/0042697, published on Feb. 16, 2017, currently U.S. patent application Ser. No. 15/334, 053, filed on Oct. 25, 2016 and titled "Implant with Arched Bone Contacting Elements," which is hereby incorporated by reference in its entirety. Also, any embodiments may make use of any of the body/support structures, members, elements, frames, plates or other structures disclosed in McShane III et al., U.S. Publication Number 2018/0110626, published on Apr. 26, 2018, and titled "Implant with Protected Fusion Zones," which is hereby incorporated by reference in its entirety and referred to as "The Protected Fusion Zones application." Also, any embodiments may make use of any of the body/support structures, members, elements, frames, plates or other structures disclosed in Nyahay et al., U.S. Publication Number 2018/0256353, published on Sep. 13, 2018, and titled "Corpectomy Implant," which is hereby incorporated by reference in its entirety.

Implantation

Figure 1:
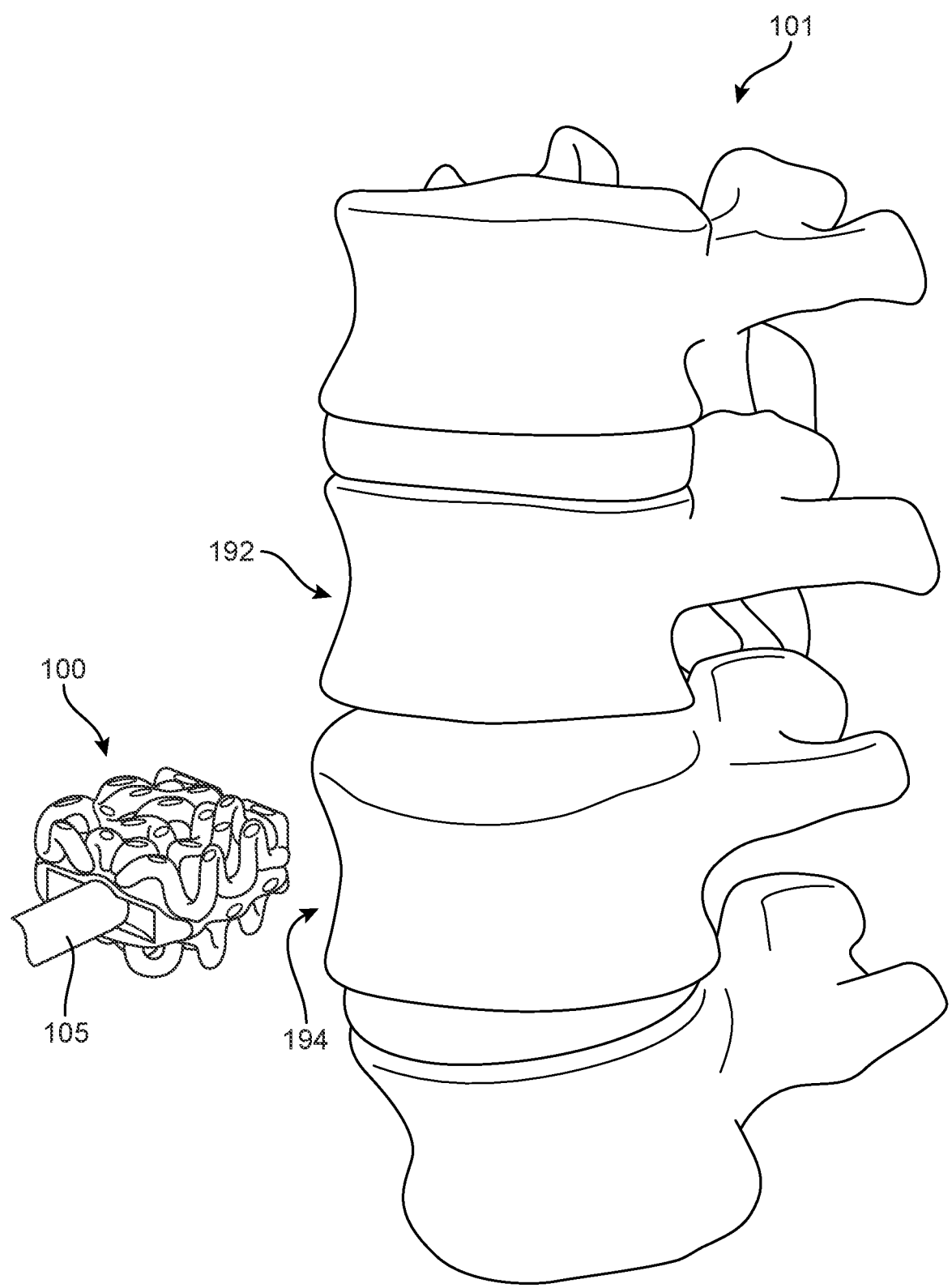
FIG. 1 is a schematic isometric view of a step of implanting a device into a spinal column, according to an embodiment.
Figure 2:
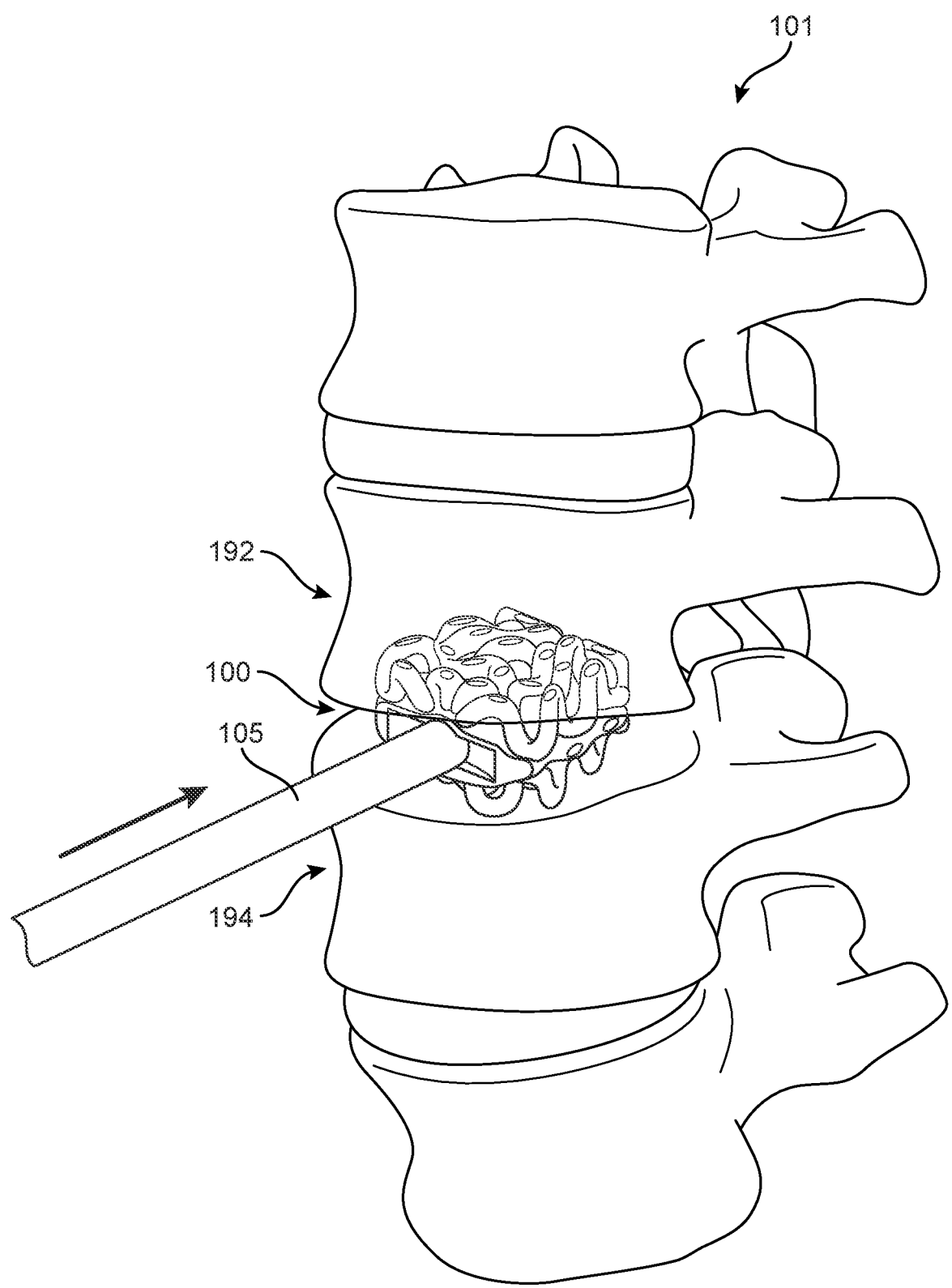
FIG. 2 is a schematic isometric view of a device implanted within a spinal column, according to an embodiment.

FIG. 1 is a schematic view of an embodiment of an implant 100. For purposes of context, implant 100 is shown adjacent to a portion of a spinal column 101. In FIG. 2, an embodiment of implant 100 is shown following insertion between two adjacent vertebrae (vertebra 192 and vertebra 194) within the spinal column 101. This insertion is facilitated by use of an insertion tool 105, which is shown schematically in FIGS. 1 and 2.

For purposes of this disclosure, implant 100 may also be referred to as a cage or fusion device. In some embodiments, implant 100 is configured to be implanted within a portion of the human body. In some embodiments, implant 100 may be configured for implantation into the spine. In some embodiments, implant 100 may be a spinal fusion implant, or spinal fusion device, which is inserted between adjacent vertebrae to provide support and/or facilitate fusion between the vertebrae.

In some embodiments, implant 100 may be inserted using an anterior lumbar interbody fusion (ALIF) surgical procedure, where the disc space is fused by approaching the spine through the abdomen. In the ALIF approach, a three-inch to five-inch incision is typically made near the abdomen and the abdominal muscles are retracted to the side. In some cases, implant 100 can be inserted through a small incision in the front or anterior side of the body. In some cases, an anterior approach may afford improved exposure to the disc space to a surgeon. The anterior approach can allow a larger device to be used for the fusion, increasing the surface area for fusion to occur and allowing for more postoperative stability. An anterior approach often makes it possible to reduce some of the deformity caused by various conditions, such as isthmic spondylolisthesis. Insertion and placement of the disc along the front of a human body can also re-establish the patient's normal sagittal alignment in some cases, giving individuals a more normal inward curve to their low back.

Introduction to Implant

For purposes of clarity, reference is made to various directional adjectives throughout the detailed description and in the claims. As used herein, the term "anterior" refers to a side or portion of an implant that is intended to be oriented towards the front of the human body when the implant has been placed in the body. Likewise, the term "posterior" refers to a side or portion of an implant that is intended to be oriented towards the back of the human body following implantation. In addition, the term "superior" refers to a side or portion of an implant that is intended to be oriented towards a top (e.g., the head) of the body while "inferior" refers to a side or portion of an implant that is intended to be oriented towards a bottom of the body. Reference is also made herein to "lateral" sides or portions of an implant, which are sides or portions facing along lateral directions of the body following implantation.

Figure 3:
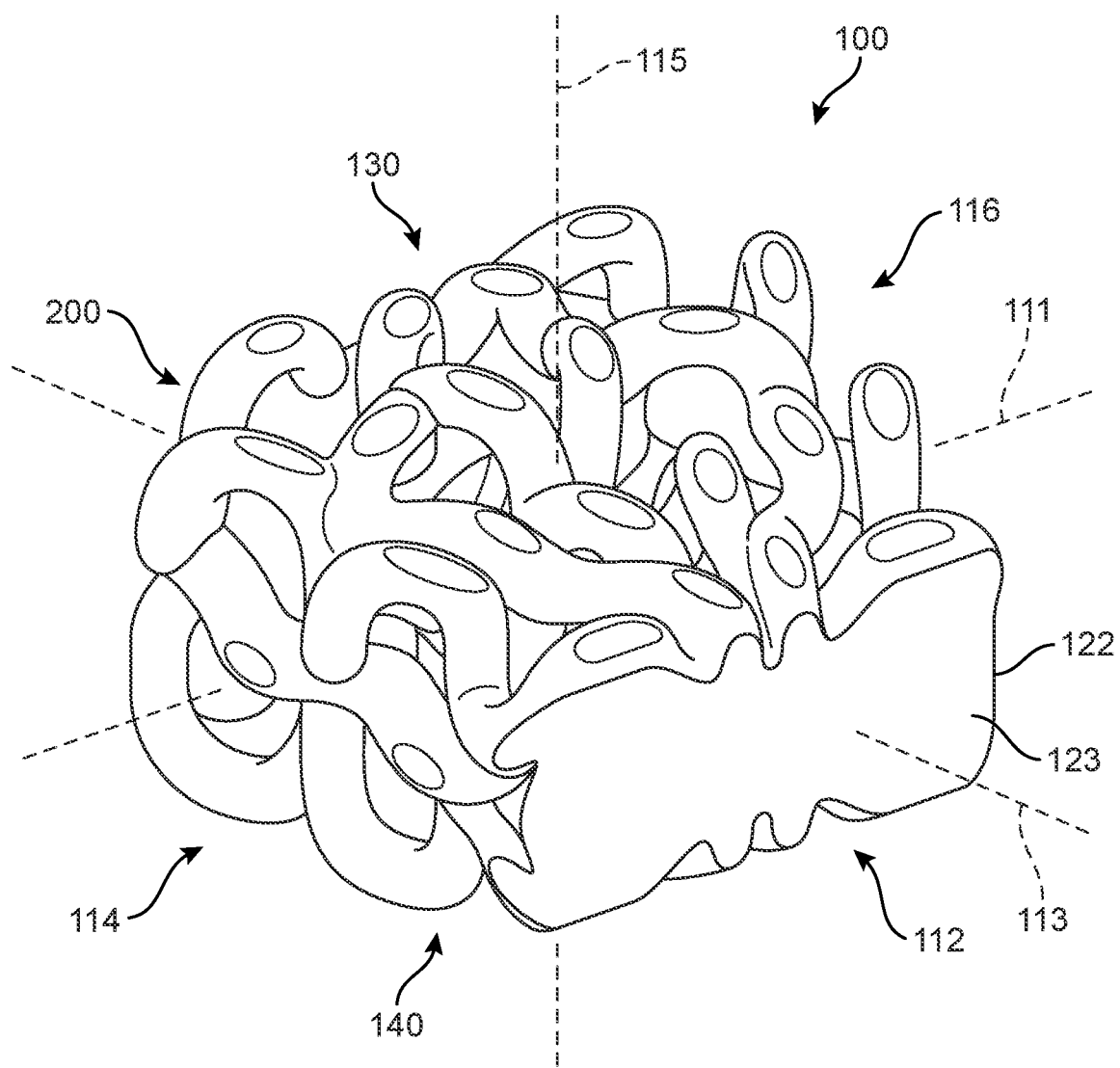
FIG. 3 is a schematic isometric view of an embodiment of an implant.
Figure 4:
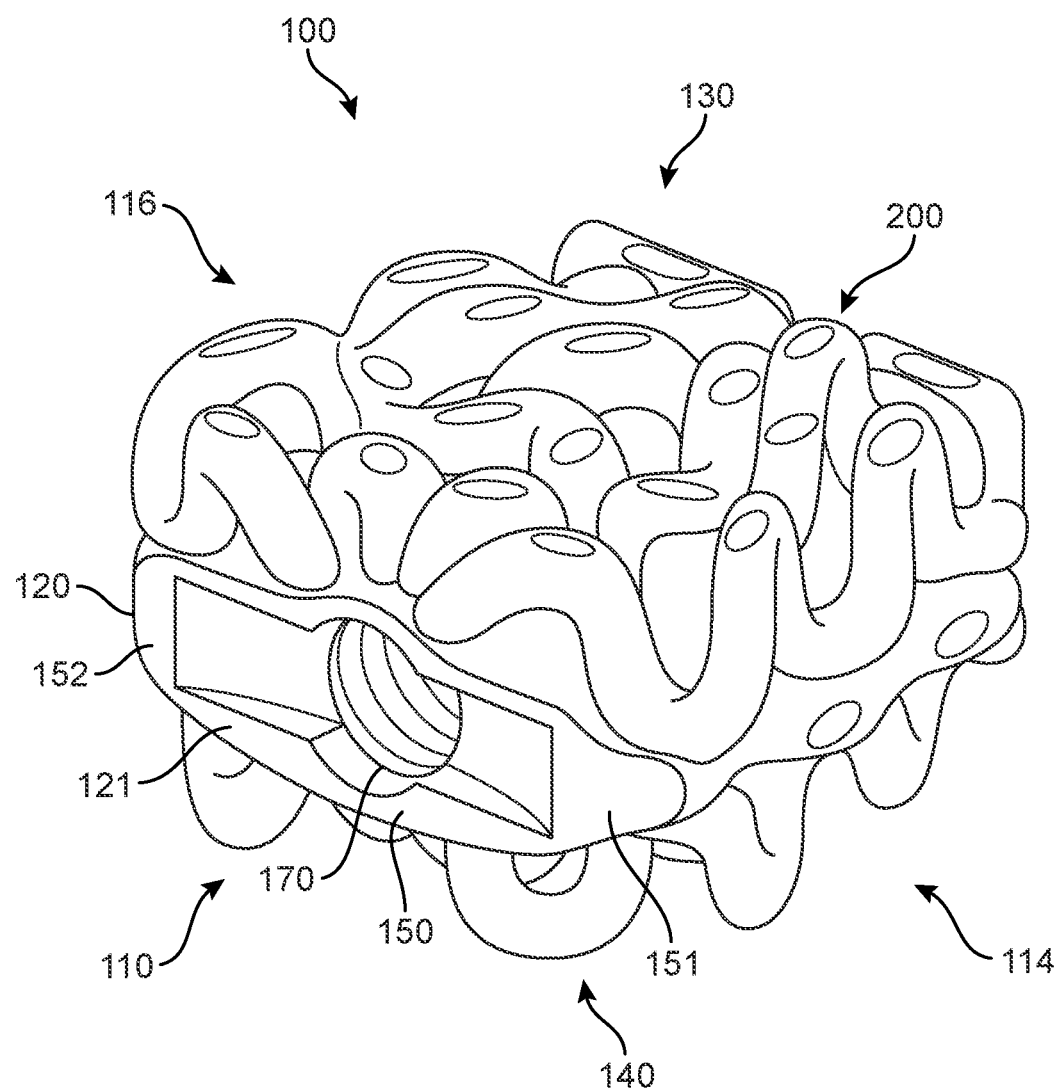
FIG. 4 is a schematic isometric view of an embodiment of an implant.

FIGS. 3-4 illustrate isometric views of an embodiment of implant 100. Specifically, FIG. 3 is a posterior isometric view while FIG. 4 is an anterior isometric view. In FIGS. 3-4, implant 100 is understood to be configured with an anterior side 110 and a posterior side 112. Implant 100 may also include a first lateral side 114 and a second lateral side 116 that extend between the posterior side 112 and the anterior side 110 on opposing sides of implant 100. Furthermore, implant 100 may also include a superior side 130 and an inferior side 140.

Implant 100 may also be associated with various edges that are located at the intersections between various sides. For example, superior side 130 and first lateral side 114 may meet at a superior-lateral edge. Likewise, inferior side 140 and first lateral side 114 may meet at an inferior-lateral edge. It may be appreciated that the term "edge" as used herein is not limited to a precise contour of implant 100 and is used instead to refer to a general region proximate the intersection of two sides or faces of implant 100.

Reference is also made to directions or axes that are relative to the implant itself, rather than to its intended orientation with regards to the body. For example, the term "distal" refers to a part that is located further from a center of an implant, while the term "proximal" refers to a part that is located closer to the center of the implant. As used herein, the "center of the implant" could be the center of mass and/or a central plane and/or another centrally located reference surface.

An implant may also be associated with various axes. Referring to FIG. 3, implant 100 may be associated with a lateral axis 111 that extends along implant 100 between first lateral side 114 and second lateral side 116. Additionally, implant 100 may be associated with a posterior-anterior axis 113 that extends between posterior side 112 and anterior side 110. Moreover, implant 100 may be associated with a vertical axis 115 (which may also be referred to as a superior-inferior axis) that extends along the thickness dimension of implant 100 and which is generally perpendicular to both lateral axis 111 and posterior-anterior axis 113.

An implant may also be associated with various reference planes or surfaces. As used herein, the term "median plane" refers to a vertical plane which passes from the anterior side to the posterior side of the implant, dividing the implant into right and left halves, or lateral halves. As used herein, the term "transverse plane" refers to a horizontal plane located in the center of the implant that divides the implant into superior and inferior halves. As used herein, the term "coronal plane" refers to a vertical plane located in the center of the implant that divides the implant into anterior and posterior halves. In some embodiments, the implant is symmetric about two planes, such as the transverse plane.

Implant 100 is comprised of one or more body members attached to one or more bone contacting elements. In the embodiments shown in FIGS. 3-4, implant 100 includes a first body member 120 and a second body member 122. Each body member generally comprises a block-like member forming a solid end or side for implant 100. In the exemplary embodiment, first body member 120 is disposed at an anterior end of implant 100, while second body member 122 is disposed at a posterior end of implant 100. Alternatively, in other embodiments, implant 100 could comprise one or more body members on either of the lateral sides extending between first body member 120 and second body member 122.

Figure 8:
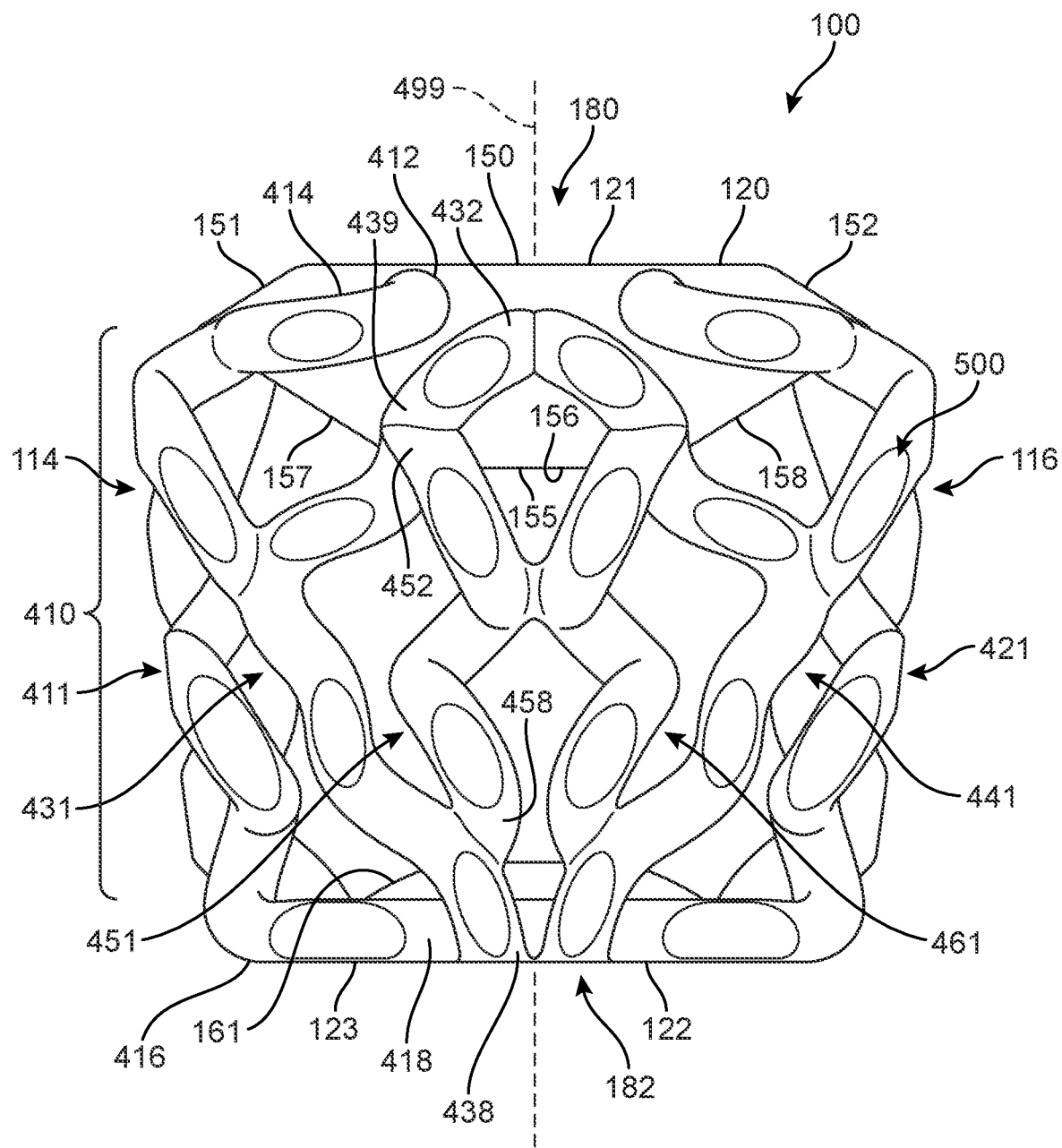
FIG. 8 is a schematic top down view of the implant of FIG. 3.

In different embodiments, the geometry of one or more body members could vary. In some embodiments, first body member 120 may comprise a solid structure including various connected faces. As seen in FIG. 4, as well as in FIG. 8, first body member 120 includes exterior surface 121 that is further comprised of a central face 150, a first angled face 151 and a second angled face 152. Additionally, first body member 120 includes an interior surface 155 with a central face 156, a first angled face 157 and a second angled face 158 (see FIG. 8). As best seen in FIG. 8, the angles between these faces are selected to provide first body member 120 with a broad and flat anterior facing side as well as to create a thicker central region 180 that can retain a fastener and/or the tip of an implantation tool.

In some embodiments, second body member 122 may comprise a solid structure with a flat exterior surface and a rounded interior surface. As seen in FIG. 8, second body member 122 includes a flat or planar exterior surface 123 and a partially rounded interior surface 161. The geometry of second body member 122 presents a smooth and flat posterior surface for insertion while creating a thicker central region along the interior of implant 100 that might retain fasteners, implantation tools or other provisions used in fastening, aligning and/or implanting the device.

In some embodiments, variations in height or vertical thickness between first body member 120 and second body member 122 may allow for an implant with hyper-lordotic angles between the inferior and superior surfaces. In other embodiments, variations in vertical thickness may be used to control the relative rigidity of the device in different locations. In other embodiments, first body member 120 and second body member 122 could have substantially similar heights.

Some embodiments can include one or more fastener receiving provisions. In some embodiments, an implant can include one or more threaded cavities. In some embodiments, a threaded cavity can be configured to mate with a corresponding threaded tip on an implantation tool or device. In other embodiments, a threaded cavity can receive a fastener for purposes of fastening an implant to another device or component in an implantation system that uses multiple implants and/or multiple components.

As best seen in FIG. 4, implant 100 includes a threaded cavity 170 disposed in first body member 120. In some embodiments, threaded cavity 170 may receive the threaded tip of an implantation tool (not shown). Such a tool could be used to drive implant 100 between adjacent vertebral bodies.

In some embodiments, first body member 120 and second body member 122 could be joined by one or more bone contacting elements. In the embodiment shown in FIGS. 3-4, implant 100 includes a plurality of bone contacting elements 200 that may be attached, and/or continuously formed (or "integrally formed") with, first body member 120 and/or second body member 122.

Figure 24:
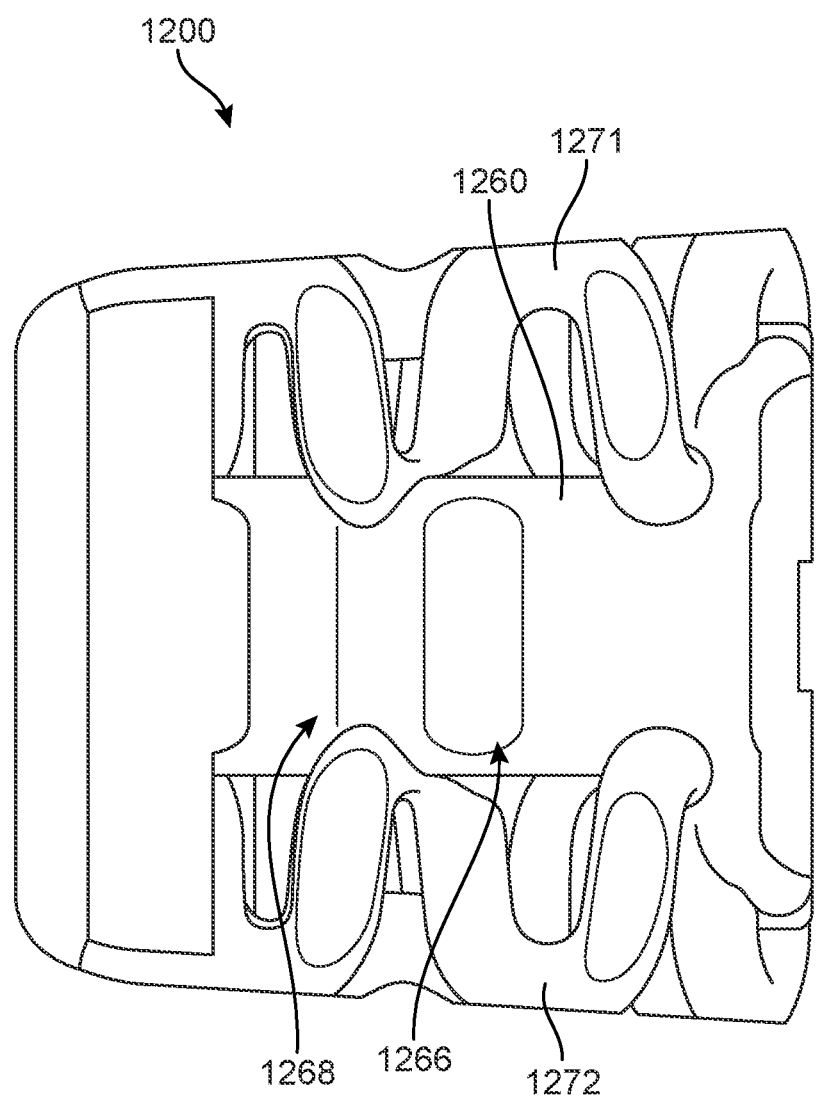
FIG. 24 is a lateral view of the implant of FIG. 21.
Figure 25:
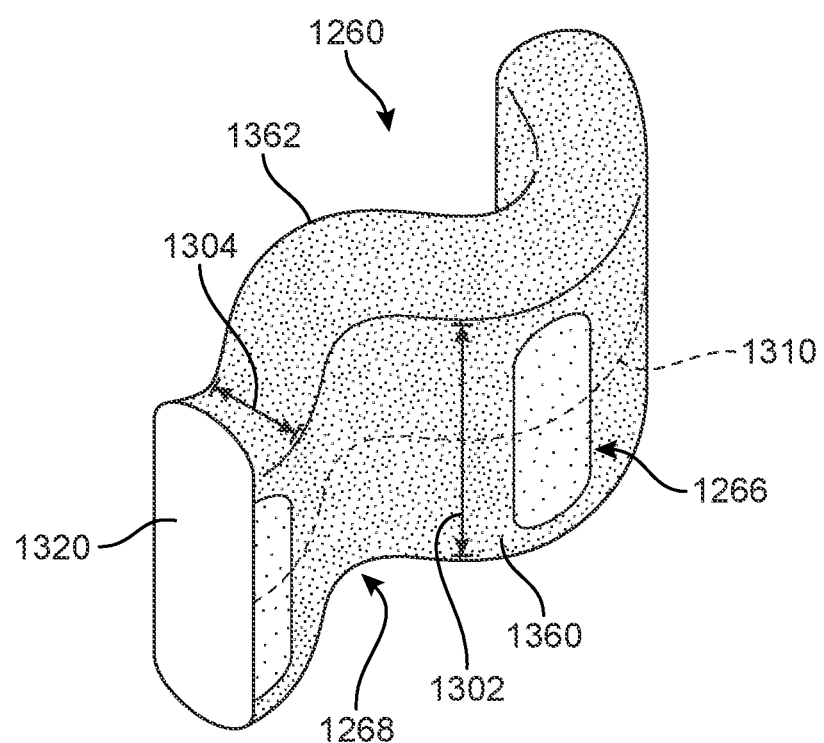
FIG. 25 is a schematic isometric view of a bone contacting element with a rectangular cross section having an undulating geometry, according to an embodiment.

As used herein, each bone contacting element comprises a distinctive member or element that spans a region or area of an implant. In some embodiments, these elements may overlap or intersect, similar to elements in a lattice or other 3D mesh structure. In other embodiments, the elements may not overlap or intersect. Some embodiments may use elongated elements, in which the length of the element is greater than its width and its thickness. For example, in embodiments where an element has an approximately circular cross-sectional shape, the element has a length greater than its diameter. In the embodiments seen in FIGS. 3-4, each bone contacting element is seen to have an approximately rounded or circular cross-sectional shape (i.e., the element has the geometry of a solid tube) along at least a portion of the element. However, in other embodiments, an element could have any other cross-sectional shape, including, but not limited to, various polygonal cross-sectional shapes (e.g., triangular, rectangular, etc.), as well as any other regular and/or irregular cross-sectional shapes. An example of an embodiment including a bone contacting element with a rectangular cross-sectional shape is shown in FIGS. 24-25 and discussed in further detail below. In some cases, for example, the cross-sectional shape of a bone contacting element could vary along its length (e.g., the diameter could change along its length).

Geometry of Bone Contacting Elements

Embodiments can include provisions for protecting bone growth along and adjacent to bone contacting elements of an implant. In some embodiments, a bone contacting element can be configured with a geometry that helps to protect new bone growth in selected regions that may be referred to as "protected fusion zones". In a protected fusion zone new bone growth may be partially protected from forces transmitted directly between vertebrae and bone contacting surfaces of an implant, thereby increasing the rate at which new bone growth may propagate through the implant.

In some embodiments, a bone contacting element can have a spiral, helical or twisted geometry that provide a series of such protected fusion zones for enhanced bone growth. In other embodiments, a bone contacting element can have a planar undulating geometry (e.g., sinusoidal) that may also create protected fusion zones. In some embodiments, an implant may include bone contacting elements with a helical geometry and other bone contacting elements with a sinusoidal, or planar undulating geometry.

Some bone contacting elements may have a generalized helical geometry. As used herein, a "generalized helical geometry" or "spiraling geometry" refers to a geometry where a part (portion, member, etc.) winds, turns, twists, rotates or is otherwise curved around a fixed path. In some cases, the fixed path could be straight. In other cases, the fixed path can be curved. In the present embodiments, for example, the fixed path is generally a combination of straight segments and curved segments.

Curves having a generalized helical geometry (also referred to as generalized helical curves) may be characterized by "coils", "turns" or "windings" about a fixed path. Exemplary parameters that may characterize the specific geometry of a generalized helical curve can include coil diameter (including both a major and minor diameter) and the pitch (i.e., spacing between adjacent coils). In some cases, the "amplitude" of a coil or loop may also be used to describe the diameter or widthwise dimension of the coil or loop. Each of these parameters could be constant or could vary over the length of a generalized helical curve.

Generalized helical curves need not be circular or even round. In some embodiments, for example, a generalized helical curve could have a linearly segmented shape (or locally polygonal shape) such that each "coil" or "turn" is comprised of straight line segments rather than arcs or other curved segments. Generalized helical curves may also include combinations of curved and straight segments. Examples of generalized helical curves are shown and described in The Protected Fusion Zones Application.

For purposes of characterizing the geometry of one or more bone contacting elements, each bone contacting element can be identified with one or more curves. Each bone contacting element may be identified with a central curve. The central curve of each bone contacting element may be defined as a curve that extends along the length (or longest dimension) of the bone contacting element such that each point along the curve is centrally positioned within the bone contacting element. In addition, each bone contacting element may be identified with one or more exterior surface curves. An exterior surface curve of a bone contacting element may be defined as a curve that extends along the length (or longest dimension) of the bone contacting element such that each point along the curve is positioned on the exterior surface.

Figure 5:
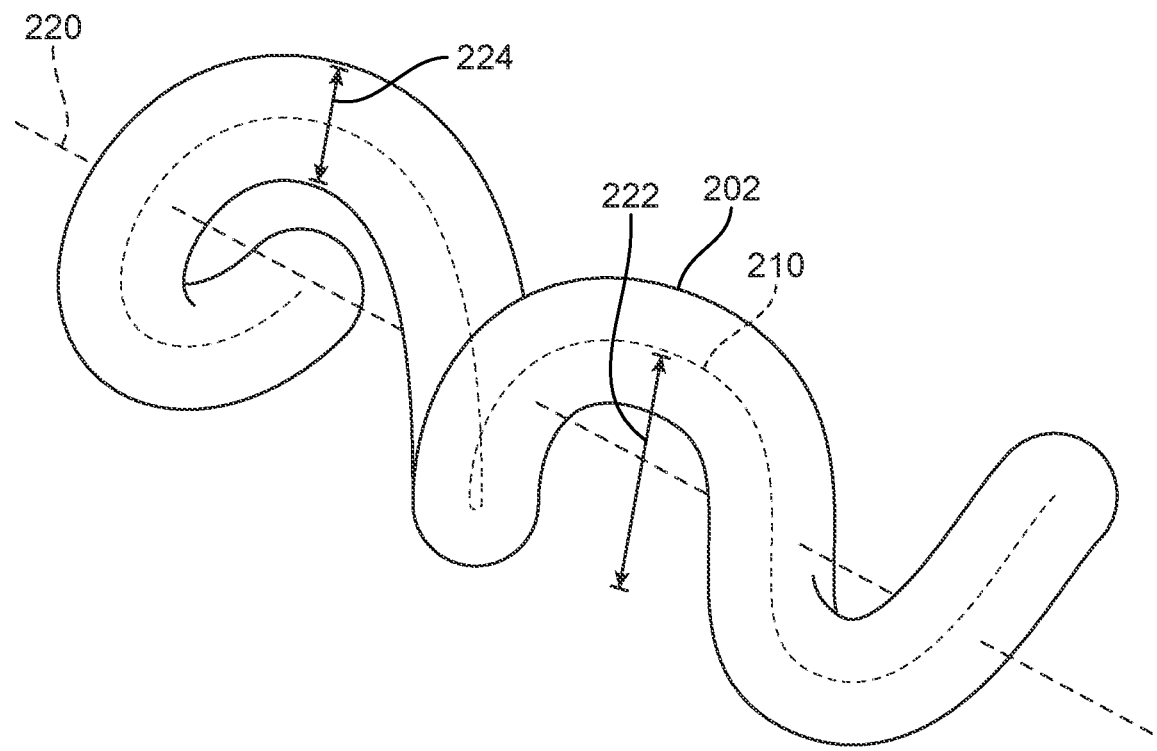
FIG. 5 is a schematic isometric view of an embodiment of a bone contacting element with a generally helical geometry.

FIG. 5 is a schematic view of an exemplary bone contacting element 202 of implant 100. For purposes of reference, bone contacting element 202 is shown in isolation from other parts of implant 100. As seen in FIG. 5, bone contacting element 202 exhibits a twisted geometry indicative of a spiral or helix (i.e., a generally helical geometry). Specifically, one or more segments of a central curve 210 of bone contacting element 202 (referred to as "winding segments") are seen to rotate or twist around fixed path 220.

In some embodiments, a bone contacting element could have a cross-sectional diameter that is larger than its winding diameter. Such an embodiment is discussed in The Protected Fusion Zones Application. In the embodiment shown in FIG. 5, bone contacting element 202 is seen to have a cross-sectional diameter 224 that is less than the winding diameter 222 of its central curve 210.

Generally, a bone contacting element may not have a generalized helical geometry through its entire length. In other embodiments, for example, its central curve may be configured with a winding segment where the central curve completes several full turns around a fixed path. Away from the winding segment, its central curve may not include any turns, twists, etc.

Although the present embodiment includes at least one bone contacting element with a winding segment that makes one or more full turns around a fixed path, other embodiments could be configured with central curves that only make partial turns around a fixed path.

While the description here has focused on the geometry of a single bone contacting element, it may be appreciated that other bone contacting elements may exhibit similar generally helical geometries. It may be further appreciated that two different bone contacting elements could have slightly different geometries, with distinct central curves that include variations in the number of windings, shape of the windings, etc.

In some embodiments, bone contacting elements may be characterized as having an undulating planar geometry. As used herein, the term "undulating planar geometry" refers to a geometry where the central curve of an element undulates (e.g., waves or oscillates) in a single plane. In other words, the central curve is an undulating planar curve. A specific example of an undulating planar curve is a sinusoidal curve, though the term undulating planar curve is not restricted to curves that undulate in a regular manner like sinusoidal curves. This undulating planar geometry is distinct from a generally helical geometry, since generally helical curves are not confined to a single plane.

Figure 6:
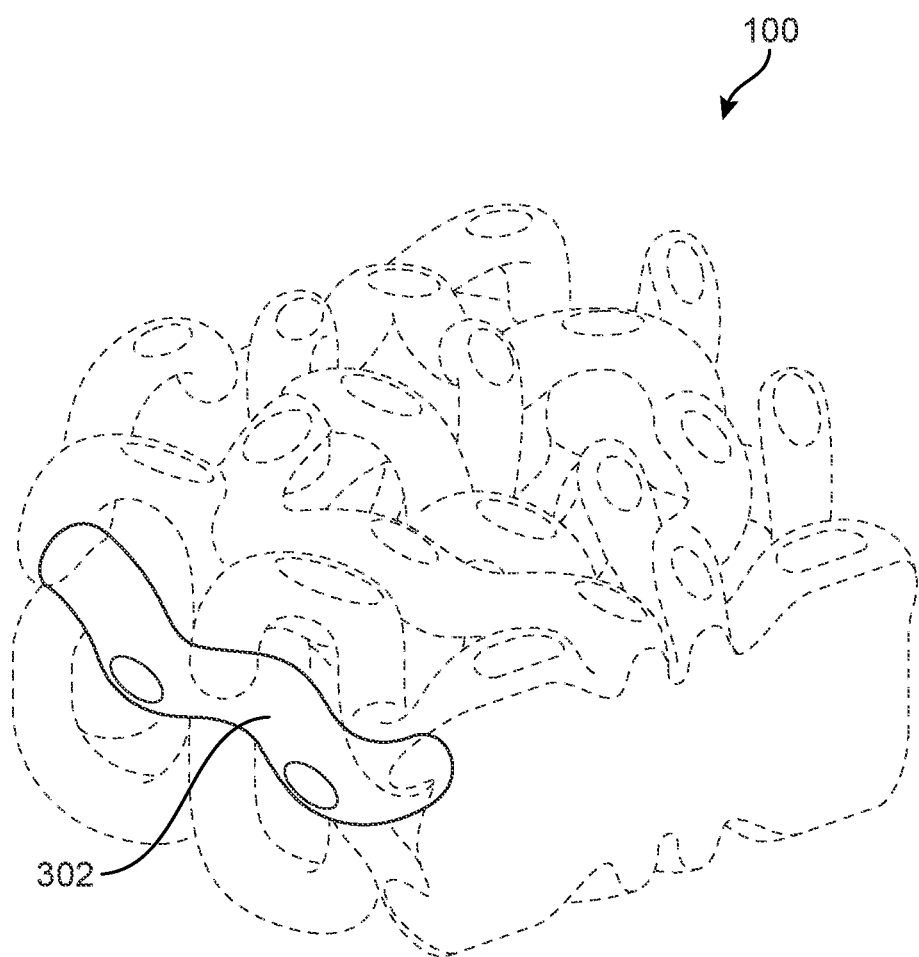
FIG. 6 is a schematic isometric view of the implant of FIG. 3, in which a single bone contacting element is highlighted.
Figure 7:
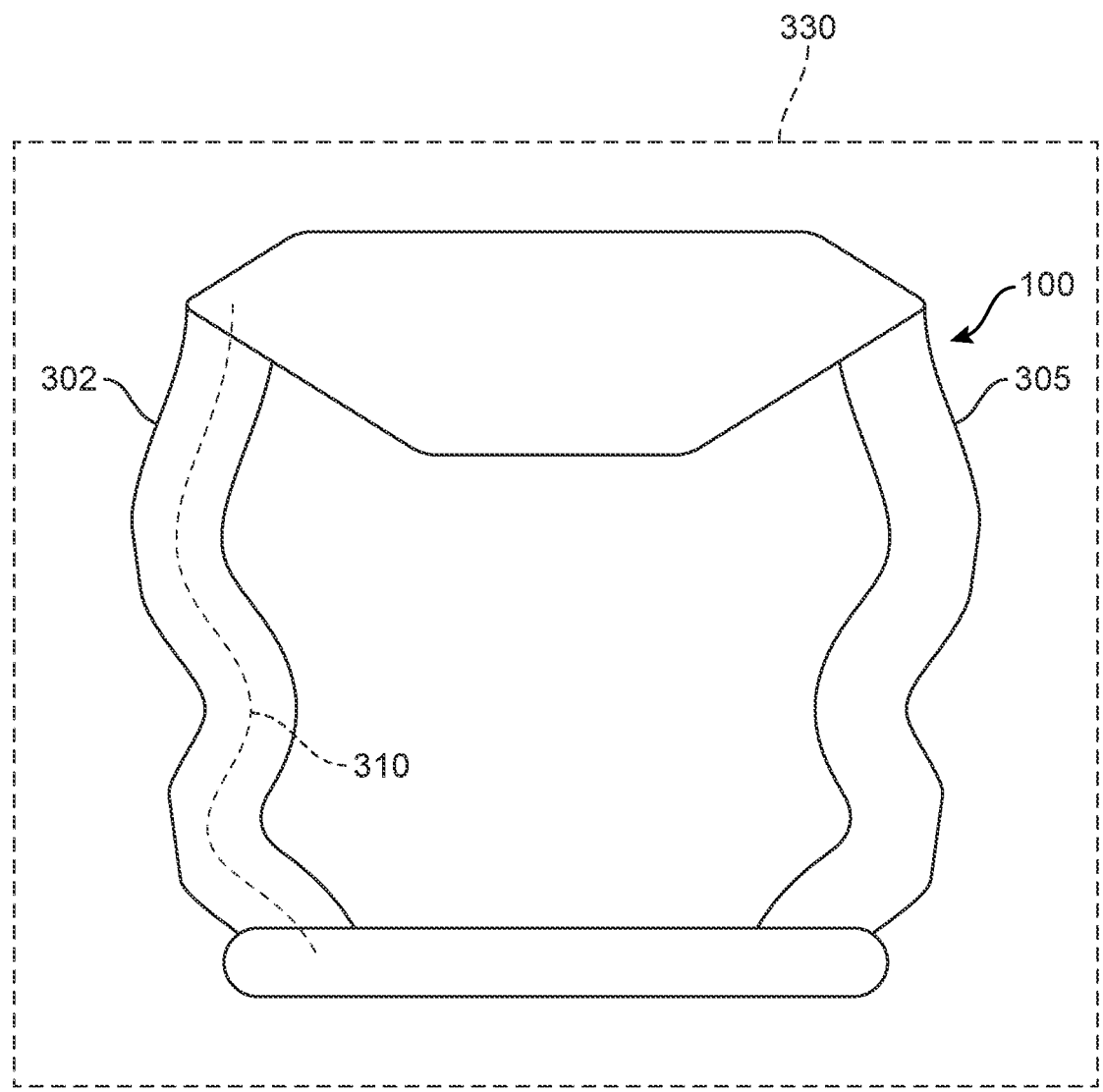
FIG. 7 is a schematic top down view of some elements of an implant, in which two of the elements have an undulating geometry, according to an embodiment.

FIG. 6 is a schematic view of a bone contacting element 302 of an implant 100. For purposes of reference, bone contacting element 302 is shown in solid lines while the remaining parts are shown in phantom. FIG. 7 is a schematic top down view of implant 100, in which bone contacting elements having generally helical geometries have been removed for purposes of clarity.

Referring to FIGS. 6-7, bone contacting element 302 exhibits an undulating planar geometry. Specifically, a central curve 310 of bone contacting element 302 is a planar curve (i.e., confined in this case to plane 330) and includes at least one undulation. Additionally, bone contacting element 305, which is disposed in an opposing lateral side of implant 100, is also seen in FIG. 7 to have an undulating planar geometry. In some embodiments, including the embodiment shown in FIG. 7, bone contacting element 302 and bone contacting element 305 may have identical geometries and may be arranged in a mirror symmetric manner about the median plane of implant 100.

It may be appreciated that in some embodiments, a bone contacting element could have a combination geometry. For example, in some cases a bone contacting element may include at least one segment with a generally helical geometry and at least one segment with an undulating planar geometry.

Arrangement of Bone Contacting Elements

Embodiments can include provisions for providing strength to an implant while maximizing the volume available within and around the implant for bone graft. Some embodiments could use generally helical bone contacting elements that are arranged in configurations that increase support throughout an implant while also increasing the number of protected fusion zones available.

Figure 9:
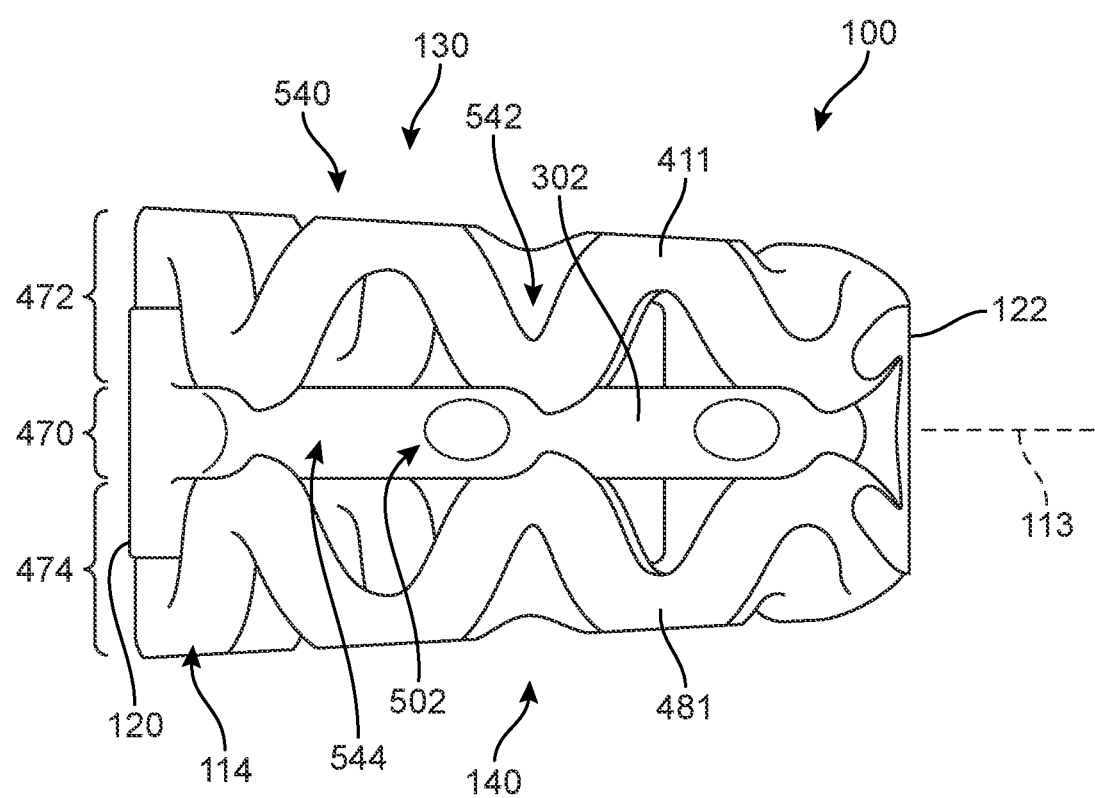
FIG. 9 is a schematic lateral view of the implant of FIG. 3.

FIG. 8 is a top down view of an embodiment of implant 100, while FIG. 9 is a side view of implant 100. Referring to FIG. 8, implant 100 includes superior set of bone contacting elements 410. Each bone contacting element in superior set of bone contacting elements 410 includes one or more segments having a generally helical geometry.

Each bone contacting element may extend between first body member 120 and second body member 122. For example, a first bone contacting element 411 extends from first body member 120 to second body member 122 along first lateral side 114 of implant 100. More specifically, first bone contacting element 411 includes a first end 412 attached at a central region 180 of first body member 120. A first undulating segment 414 of first bone contacting element 411 extends from central region 180 to first lateral side 114, at which point first bone contacting element 411 turns to extend down along first lateral side 114. At second body member 122, first bone contacting element 411 turns again and a second undulating segment 416 extends from the first lateral side 114 at second body member 122 to central region 182 of second body member 122. Here, first bone contacting element 411 terminates at a second end 418.

Second bone contacting element 421 extends along the opposing second lateral side 116 of implant 100. Specifically, in the embodiment shown in FIG. 8, second bone contacting element 421 is configured in a mirror symmetric manner from first bone contacting element 411 about the median plane (represented in FIG. 8 by median plane axis 499).

Adjacent to first bone contacting element 411 is a third bone contacting element 431. A first end 432 of third bone contacting element 431 is attached at central region 180 of first body member 120. In some embodiments, first end 432 is attached closer to the median plane than first end 412 of first bone contacting element 411. From first end 432, third bone contacting element 431 extends both laterally and longitudinally until it contacts first bone contacting element 411. At this contact point, third bone contacting element 431 turns and extends to second body member 122, with a second end 438 attached to second body member 122. As seen in FIG. 8, second end 438 of third bone contacting element 431 is disposed closer to the median plane than second end 418 of first bone contacting element 411 is to the median plane.

Fourth bone contacting element 441 extends along the opposing side of implant 100 from third bone contacting element 431. Specifically, in the embodiment shown in FIG. 8, fourth bone contacting element 441 is configured in a mirror symmetric manner from third bone contacting element 431 about the median plane.

Adjacent to third bone contacting element 431 is fifth bone contacting element 451. A first end 452 of fifth bone contacting element 451 extends from a recessed region 439 of third bone contacting element 431 and continues longitudinally (while spiraling) to second body member 122. A second end 458 of fifth bone contacting element 451 attaches to central region 182 of second body member 122. Alternatively, in some embodiments, second end 458 of fifth bone contacting element 451 may attach directly to a portion of third bone contacting element 431.

Sixth bone contacting element 461 extends along the opposing side of implant 100 from fifth bone contacting element 451. Specifically, in the embodiment shown in FIG. 8, sixth bone contacting element 461 is configured in a mirror symmetric manner from fifth bone contacting element 451 about the median plane.

As seen in FIG. 8, fifth bone contacting element 451 may be positioned closer to the median plane than first bone contacting element 411 and third bone contacting element 431. Similarly, sixth bone contacting element 461 may be positioned closer to median plane than fourth bone contacting element 441 and second bone contacting element 421. Thus, fifth bone contacting element 451 and sixth bone contacting element 461 are positioned to provide support through the center of implant 100 (where center here refers to the center with respect to the lateral direction of the implant).

Using this exemplary configuration, first bone contacting element 411 and second bone contacting element 421 provide support along the lateral sides of implant 100. Fifth bone contacting element 451 and sixth bone contacting element 461 provide support at the center of implant 100. Furthermore, the present configuration uses third bone contacting element 431 and fourth bone contacting element 441 as additional supports that distribute loads between the outermost bone contacting elements (i.e., first bone contacting element 411 and second bone contacting element 421) and the innermost bone contacting elements (i.e., fifth bone contacting element 451 and sixth bone contacting element 461). Using helical elements to facilitate central and lateral support rather than straight or simply curved beams or struts allows for an increase in the number of protected fusion zones provided throughout implant 100.

It may be understood that in some embodiments, one or more bone contacting elements from a superior side of an implant may contact one or more bone contacting elements from an inferior side of an implant. In some embodiments, centrally positioned bone contacting elements on the superior and inferior sides of an implant may connect with one another adjacent the transverse plane. In one embodiment, for example, fifth bone contacting element 451 and sixth bone contacting element 461 could include portions that extend to the transverse plane and connect with corresponding portions of bone contacting elements disposed on the inferior side of implant 100. In some cases, such connections may help improve vertical strength, especially in a central region of the implant.

To provide protected fusion zones along the lateral sides of a device while reinforcing the implant along the transverse plane, embodiments can use bone contacting elements that undulate in a single plane. As seen in FIG. 9, first lateral side 114 of implant 100 incorporates bone contacting element 302. Bone contacting element 302 has an undulating planar geometry as previously discussed and shown in FIGS. 6-7.

Referring to FIG. 9, bone contacting element 302 extends from first body member 120 to second body member 122 on first lateral side 114. Moreover, bone contacting element 302 is disposed between, and provides support to, first bone contacting element 411 on superior side 130 as well as a corresponding bone contacting element 481 on inferior side 140.

Bone contacting element 305 extends from first body member 120 to second body member 122 on lateral side 116 (see FIG. 7). Moreover, bone contacting element 305 is disposed between, and provides support to, second bone contacting element 421 on superior side 130 as well as a corresponding bone contacting element (not shown) on inferior side 140.

Using this arrangement, bone contacting element 302 and bone contacting element 305 provide peripheral support for implant 100. Specifically, these elements provide attachment points to support helical bone contacting elements located on the lateral sides of implant 100. Moreover, using elements that undulate in the transverse plane of implant 100 also creates protected fusion zones for new bone growth on the lateral sides of implant 100.

The use of helical elements on the superior and inferior sides of an implant along with undulating planar elements along the transverse plane provides a unique layered structure for implant 100. As best seen in FIG. 9, some embodiments may be characterized by a central layer 470 of undulating planar bone contacting elements sandwiched between a superior layer 472 of generally helical bone contacting elements and an inferior layer 474 of generally helical bone contacting elements.

In some embodiments, superior layer 472 and inferior layer 474 may be mirror symmetric about the transverse plane of implant 100. Moreover, each of superior layer 472 and inferior layer 474 may include six spirals each, as well as three spirals per quadrant.

Embodiments may include one or more bone contacting regions. Bone contacting regions may be regions along a bone contacting element and/or body member that are configured to directly contact a vertebral body or other adjacent bone or tissue following implantation. These regions may comprise the distal most surfaces of an implant, including the distal most surfaces on the superior, inferior and lateral sides of the implant.

In different embodiments, the geometry of one or more bone contacting regions could vary. In some embodiments, bone contacting regions could be relatively smooth regions. In some cases, bone contacting regions could be relatively flat regions. In other embodiments, a bone contacting region may be curved. In some cases, the bone contacting region could have a curvature that matches the curvature of the adjacent surface regions of the outer member. In other cases, the distal surface region could have a different curvature (e.g., more convex) than adjacent surface regions of the outer member.

As seen in FIG. 8, implant 100 includes a first plurality of bone contacting regions 500 disposed along the generally helical superior set of bone contacting elements 410. First plurality of bone contacting regions 500 may be disposed on the distal most portions of superior set of bone contacting elements 410, and thereby configured to directly contact a corresponding vertebral surface following implantation. Although not shown, bone contacting elements on inferior side 140 of implant 100 may likewise include a plurality of bone contacting regions configured to directly contact an opposing vertebral surface.

As seen in FIG. 9, implant 100 includes a second plurality of bone contacting regions 502 that are disposed on undulating planar bone contacting element 302. Second plurality of bone contacting regions 502 may be disposed on the distal most portions of bone contacting element 302, and thereby configured to directly contact any tissue disposed against the lateral sides of implant 100 following implantation. Although not shown, bone contacting element 305 on an opposing lateral side of implant 100 may likewise include a plurality of bone contacting regions.

In different embodiments, the number of bone contacting regions could vary. In some embodiments, an implant could include between 10 and 100 bone contacting regions. In other embodiments, an implant could include less than 10 bone contacting regions. In still other embodiments, an implant could include more than 100 bone contacting regions. In the exemplary embodiment of FIGS. 8-9, implant 100 may include approximately 42 to 46 bone contacting regions. Specifically, implant 100 includes approximately 20 bone contacting regions on superior side 130, approximately 20 bone contacting regions on inferior side 140, approximately 1-3 bone contacting regions on first lateral side 114 and approximately 1-3 bone contacting regions on second lateral side 116.

Using bone contacting elements having generally helical and/or undulating planar geometries may help facilitate new bone growth since elements with these geometries naturally incorporate one or more protected fusion zones. These protected fusion zones generally occur at locations along the bone contacting element that are proximally located with respect to the distal-most bone contacting surfaces (i.e., bone contacting regions).

Connections Between Bone Contacting Elements

Figure 10:
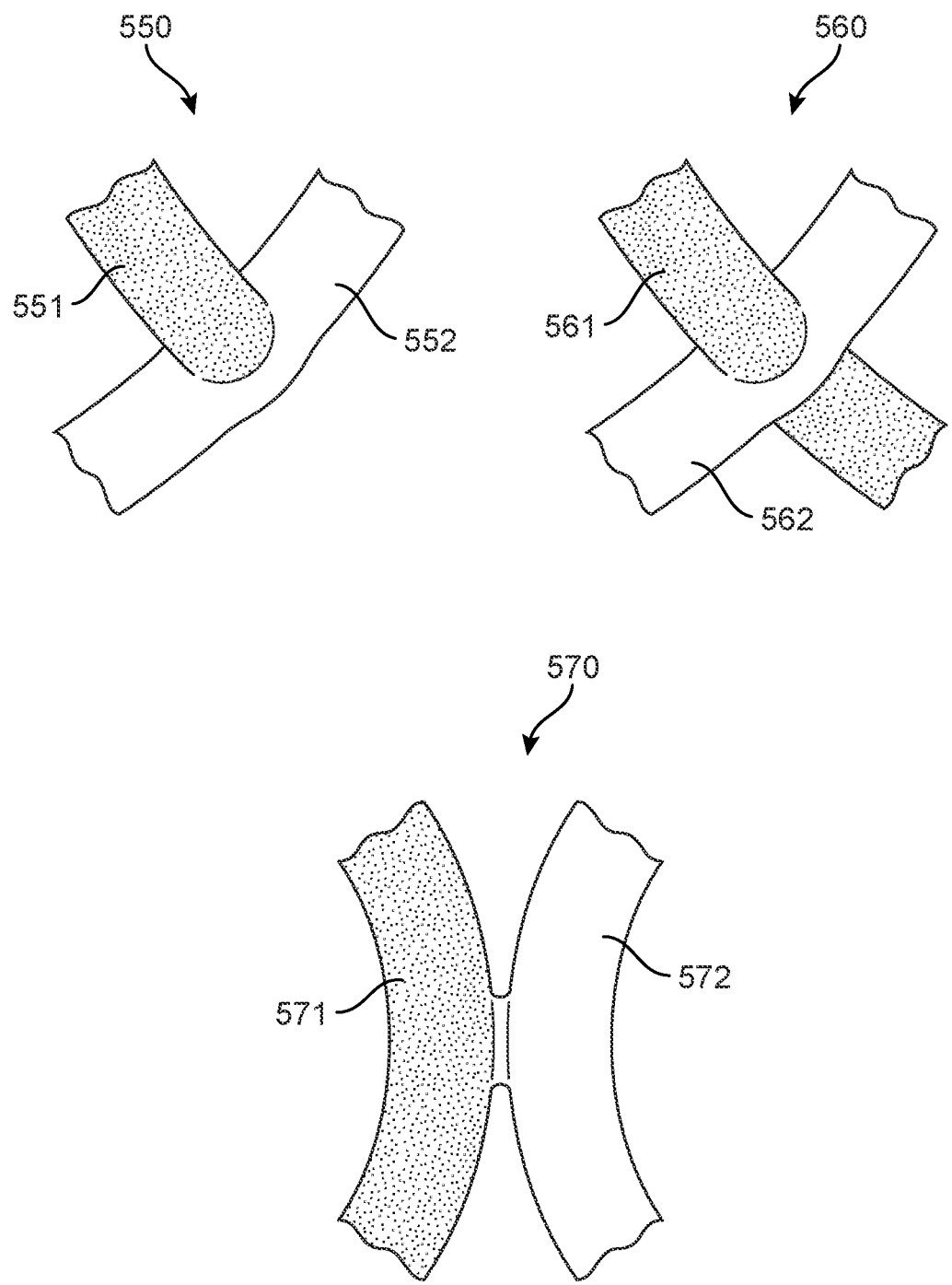
FIG. 10 is a schematic view of several types of connections between bone contacting elements, according to an embodiment.

In different embodiments, bone contacting elements may connect with one another in various ways. FIG. 10 is a schematic view of several different types of connections between bone contacting elements. As seen in FIG. 10, in one exemplary type of connection 550, the end of one bone contacting element 551 may connect to another bone contacting element 552. In another exemplary type of connection 560, two bone contacting elements (i.e., element 561 and element 562) may intersect such that they pass through or across one another. In still another exemplary type of connection 570, a bone contacting element 571 and a bone contacting element 572 may form a tangential connection, in which the elements touch only along their sidewalls.

Figure 11:
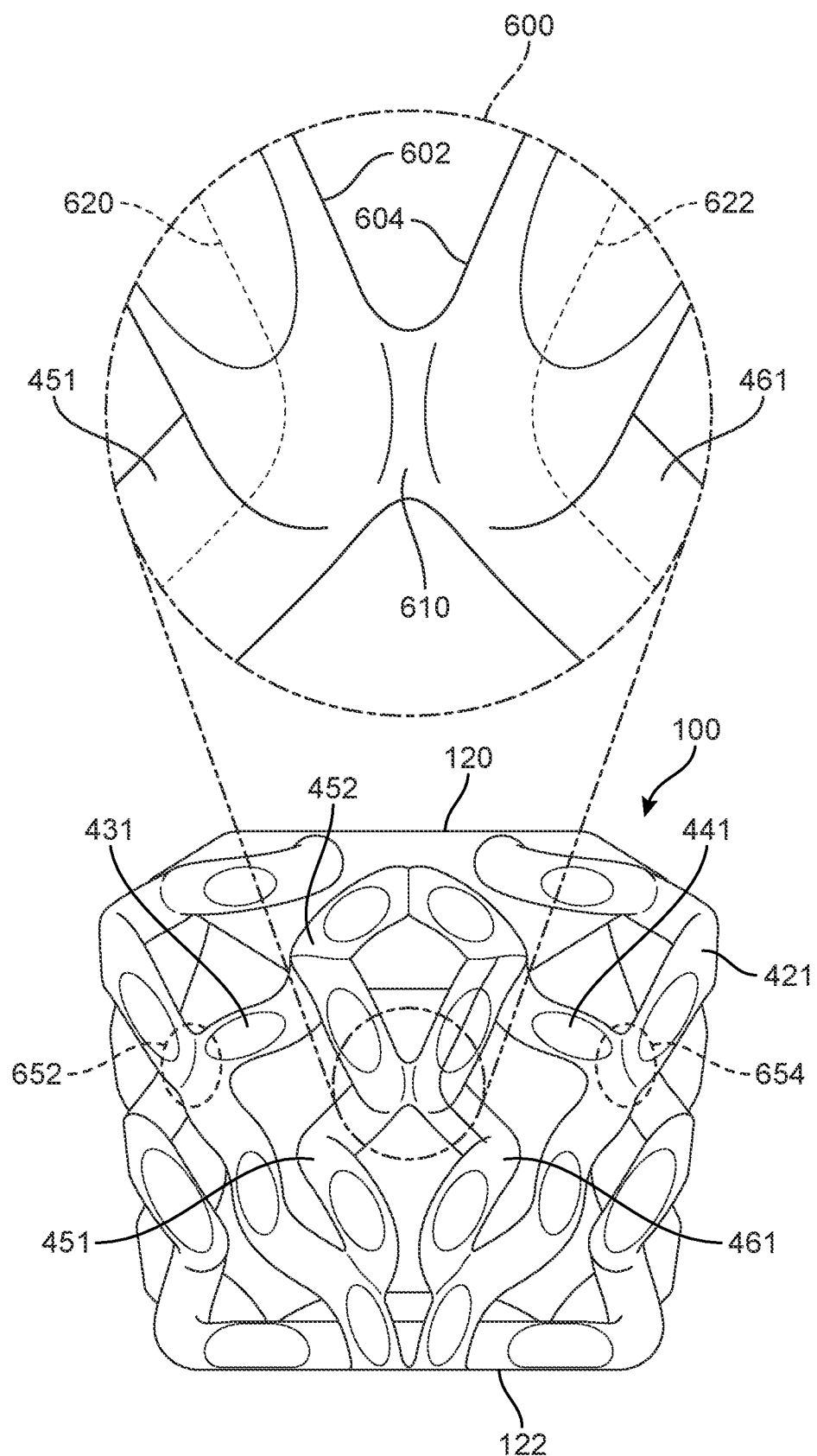
FIG. 11 is a schematic top down view of the implant of FIG. 3, in which an enlarged view of a connection region is also shown.

FIG. 11 is a schematic view of an embodiment of implant 100 including an enlarged schematic view of a connecting region 600 where two bone contacting elements contact one another. Referring to FIG. 11, the enlarged region includes portions of fifth bone contacting element 451 and sixth bone contacting element 461. Here, fifth bone contacting element 451 includes a sidewall 602 and sixth bone contacting element 461 includes a sidewall 604. As used herein, the term "sidewall" refers to the outer wall or outer surface of the bone contacting element, which extends between opposing ends of the bone contacting element.

As seen in FIG. 11, sidewall 602 of fifth bone contacting element 451 and sidewall 604 of sixth bone contacting element 461 turn towards one another and touch before turning away from one another again. Specifically, sidewall 602 and sidewall 604 come into contact at connecting portion 610. Additionally, sidewall 602 and sidewall 604 are separated at all locations away from connecting region 600.

In some cases, bone contacting elements may intersect in a perpendicular manner. An example occurs where first end 452 of fifth bone contacting element 451 attaches to a portion of third bone contacting element 431. In contrast, in connecting region 600 fifth bone contacting element 451 and sixth bone contacting element 461 are tangential to one another. Specifically, central curve 620 of fifth bone contacting element 451 and central curve 622 of sixth bone contacting element 461 are approximately parallel at connecting portion 610.

Using tangential connections between bone contacting elements allows for increased lateral strength while minimizing or eliminating the need for separate support elements that run laterally across an implant. Specifically, in the embodiment of FIG. 11, fifth bone contacting element 451 and sixth bone contacting element 461 may be attached, and provide lateral support, to one another while also extending primarily in a longitudinal direction between first body member 120 and second body member 122. Similarly, other bone contacting elements of implant 100 may be configured such that they connect along their sidewalls. For example, in the embodiment shown in FIG. 11, implant 100 includes second tangential connecting portion 652 between first bone contacting element 411 and third bone contacting element 431; and third tangential connecting portion 654 between third bone contacting element 431 and fifth bone contacting element 451. It may be appreciated that similar tangential connections may be present on an inferior side of implant 100.

Figure 12:
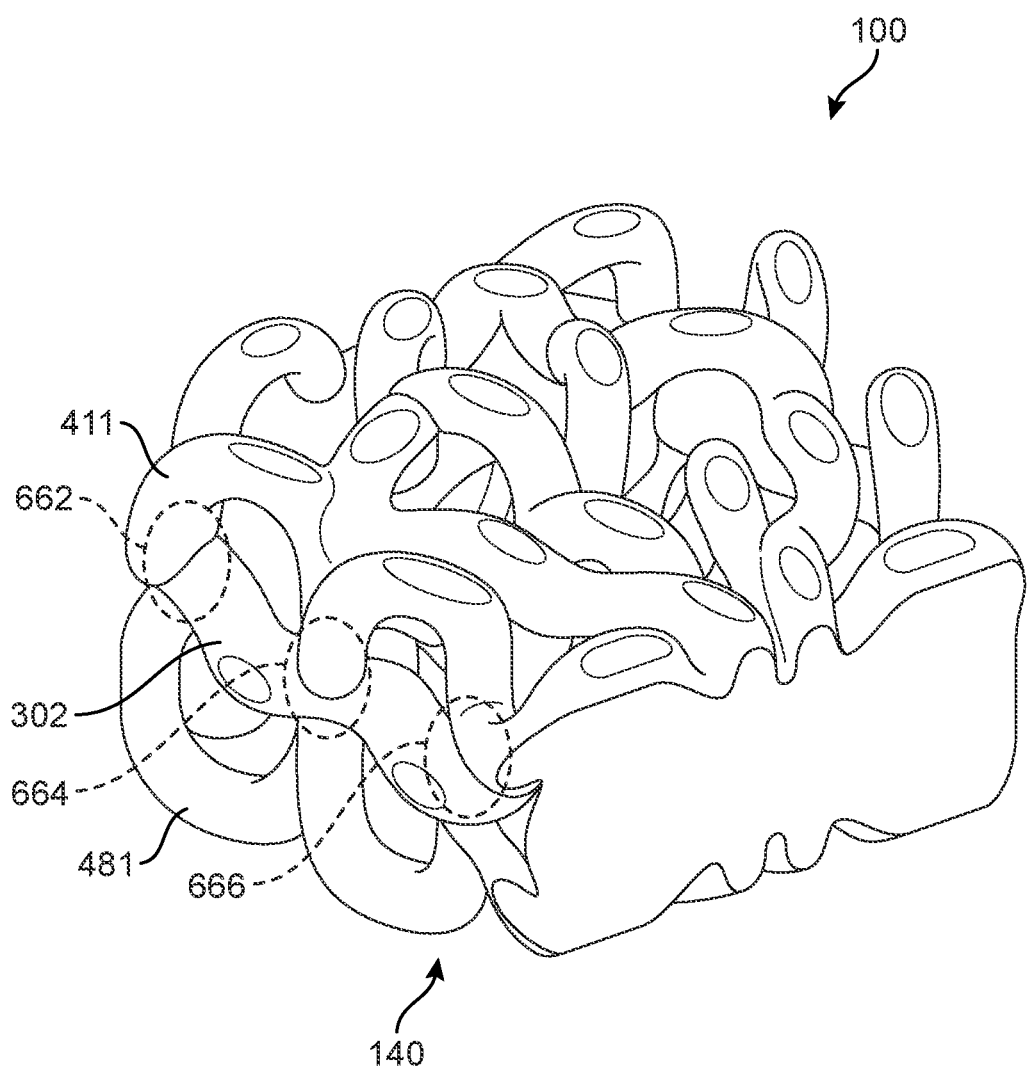
FIG. 12 is a schematic isometric view of the implant of FIG. 3, in which several connection regions are highlighted.

In some embodiments, tangential connections may occur between generally helical bone contacting elements and undulating planar bone contacting elements. Referring to FIG. 12, which shows a schematic isometric view of implant 100, several exemplary tangential connections are highlighted. These include tangential connection 662, tangential connection 664 and tangential connection 666, which are all tangential connections between first bone contacting element 411 and bone contacting element 302. Additional tangential connections may occur between bone contacting element 302 and bone contacting element 481 on inferior side 140 of implant 100. It may be appreciated that similar tangential connections between helical elements and undulating planar elements may be present on the opposing second lateral side 116.

In some embodiments, there may be a relationship between the oscillation patterns of a generally helical element and an adjacent undulating planar element. In some cases, the "peaks" (i.e., distal-most portions) of a helical element may correspond with the "peaks" (i.e., distal-most portions) of an undulating planar element. For example, the peaks of both kinds of elements may have a similar longitudinal position along the posterior-anterior axis 113. In other cases, the peaks could be offset such that the peaks of a helical element correspond to the "troughs" (i.e., proximal-most portions) of an undulating planar element. In still other cases, the peaks could be offset such that the peaks of a helical element lie somewhere between the peaks and troughs of an undulating planar element.

In the embodiment shown in FIG. 9, bone contacting element 411 includes several bone contacting regions 540, which are associated with the peaks or distal-most portions of first bone contacting element 411. Likewise, bone contacting element 302 includes several second plurality of bone contacting regions 502, which are associated with the peaks or distal-most portions of bone contacting element 302. Here, the peaks are seen to be offset, with second plurality of bone contacting regions 502 having different longitudinal positions from bone contacting regions 540. With this arrangement, the corresponding protected fusion zones 542 in first bone contacting element 411 are offset from the protected fusion zones 544 in bone contacting element 302. This may help prevent new bone growth from initially growing along lateral bands (i.e., bands with a common longitudinal position) along the lateral sides of implant 100.

In different embodiments, the amplitude (or winding diameter) of generally helical bone contacting elements can vary. In some embodiments, a first generally helical bone contacting element could have a larger amplitude than a second generally helical bone contacting element. In other embodiments, each generally helical bone contacting element in an implant could have a similar amplitude.

Figure 13:
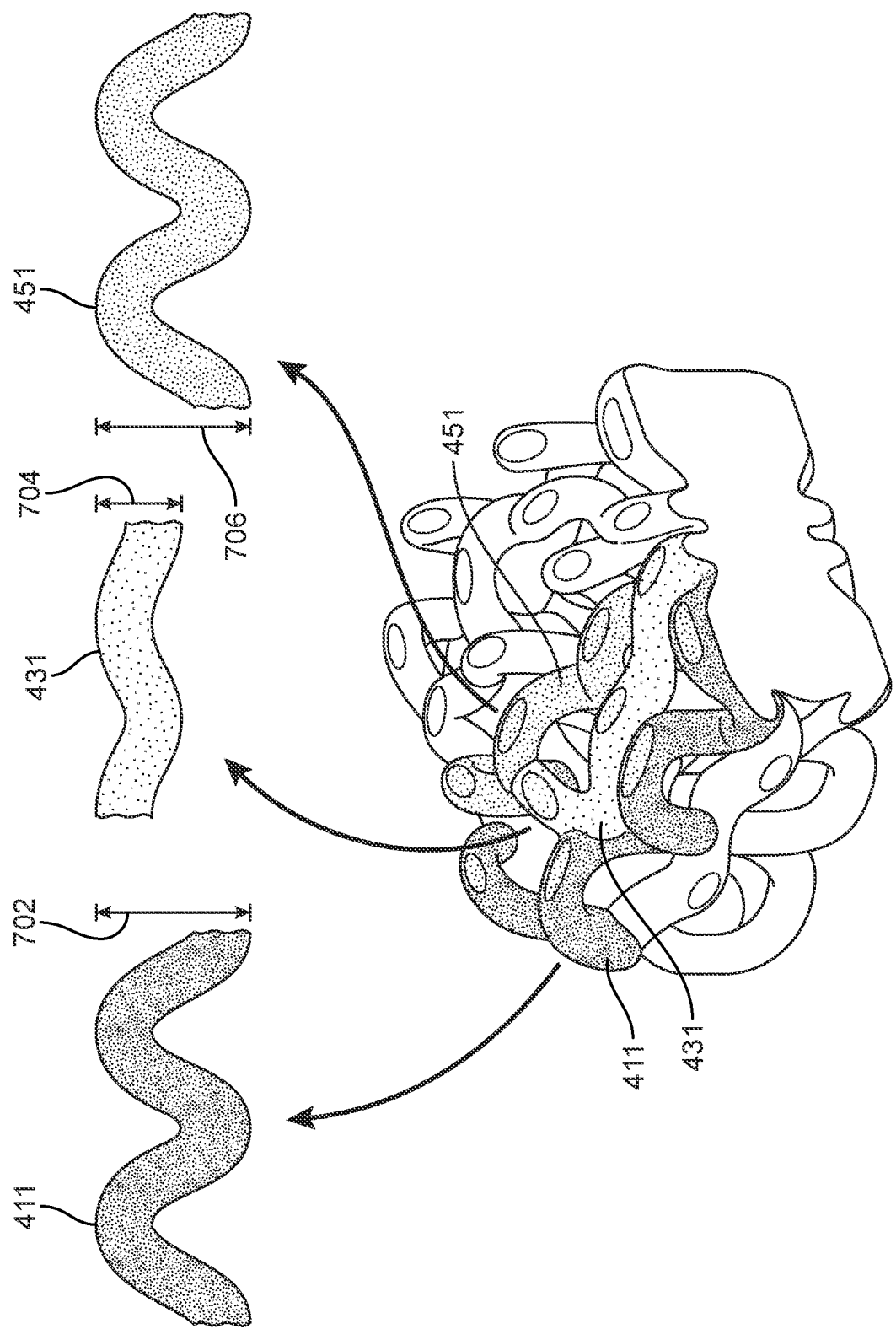
FIG. 13 is a schematic isometric view of the implant of FIG. 3, in which the relative amplitudes of three adjacent bone contacting elements are schematically compared.

In one embodiment, shown in FIG. 13, first bone contacting element 411 has an amplitude 702 (or winding diameter) that is greater than an amplitude 704 of third bone contacting element 431. In addition, fifth bone contacting element 451 is seen to have an amplitude 706 that is also greater than amplitude 704 of third bone contacting element 431. This arrangement allows third bone contacting element 431, with its relatively smaller amplitude, to primarily distribute lateral loads between first bone contacting element 411 on the lateral side of implant 100 and fifth bone contacting element 451, which is centrally located within implant 100.

Surface Texturing

Embodiments can include provisions for texturing one or more surfaces of an implant. Such texturing can increase or otherwise promote bone growth and/or fusion to surfaces of the implant. In some embodiments, bone contacting elements and/or sections of a body may be textured.

In some embodiments, the surface structure of one or more regions of an implant may be roughened or provided with irregularities. Generally, this roughened structure may be accomplished through the use of acid etching, bead or grit blasting, sputter coating with titanium, sintering beads of titanium or cobalt chrome onto the implant surface, as well as other methods. This can result in a prosthesis with a surface roughness with about 3-5 microns of roughness peak to valley. However, in some embodiments, the surface roughness may be less than 3-5 microns peak to valley, and in other embodiments, the surface roughness may be greater than 3-5 microns peak to valley.

Figure 14:
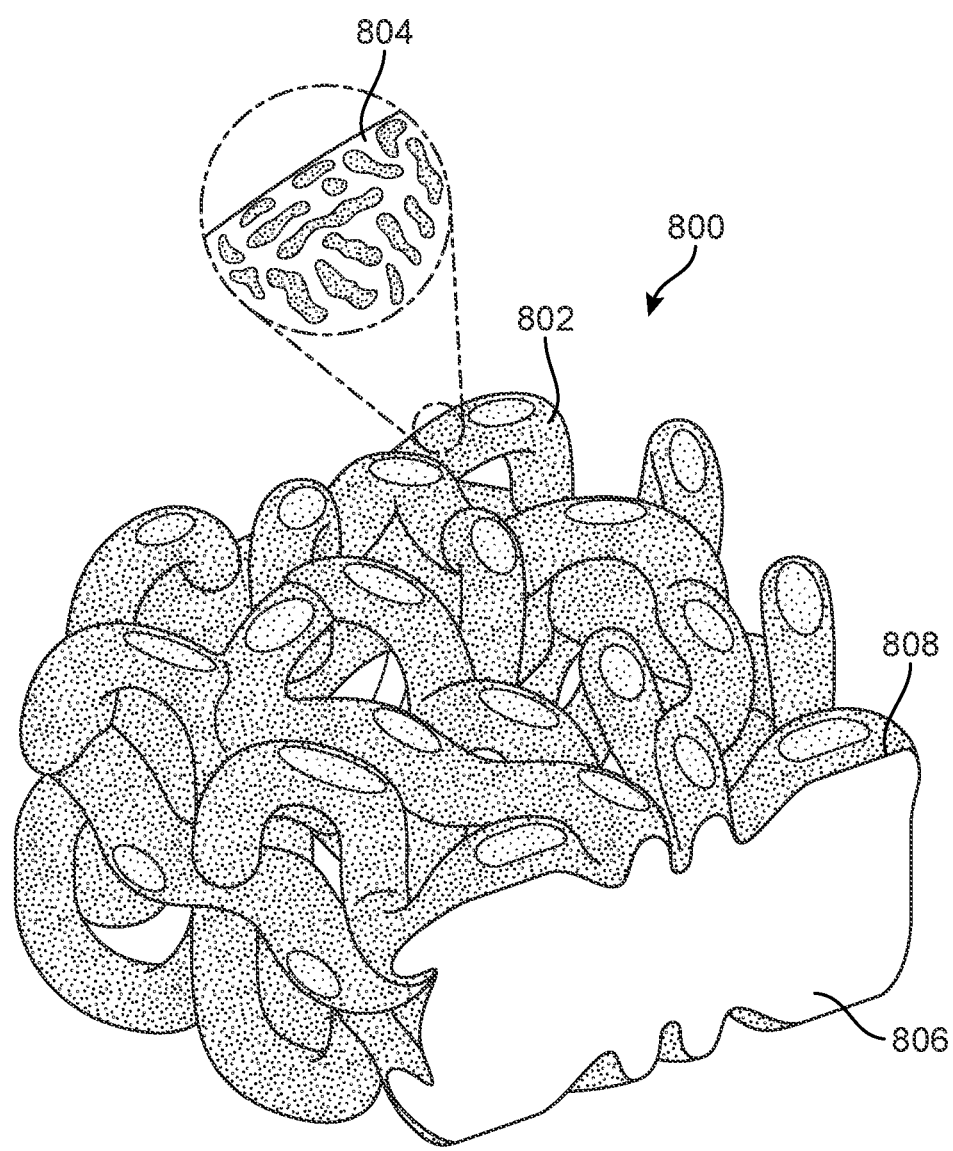
FIG. 14 is a schematic view of an implant with a textured surface for promoting bone growth, according to an embodiment.
Figure 15:
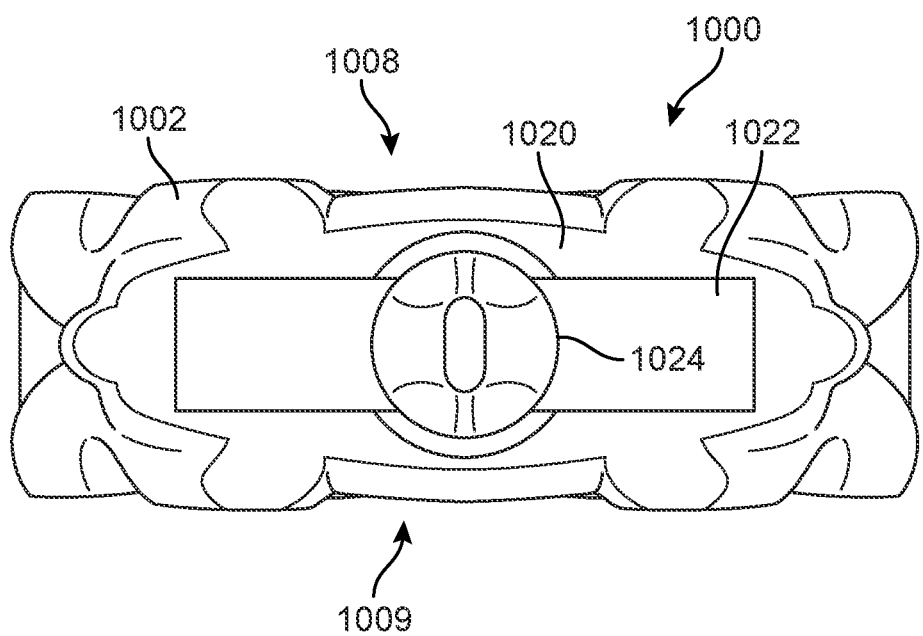
FIG. 15 is a schematic anterior view of another embodiment of an implant with bone contacting elements.
Figure 16:
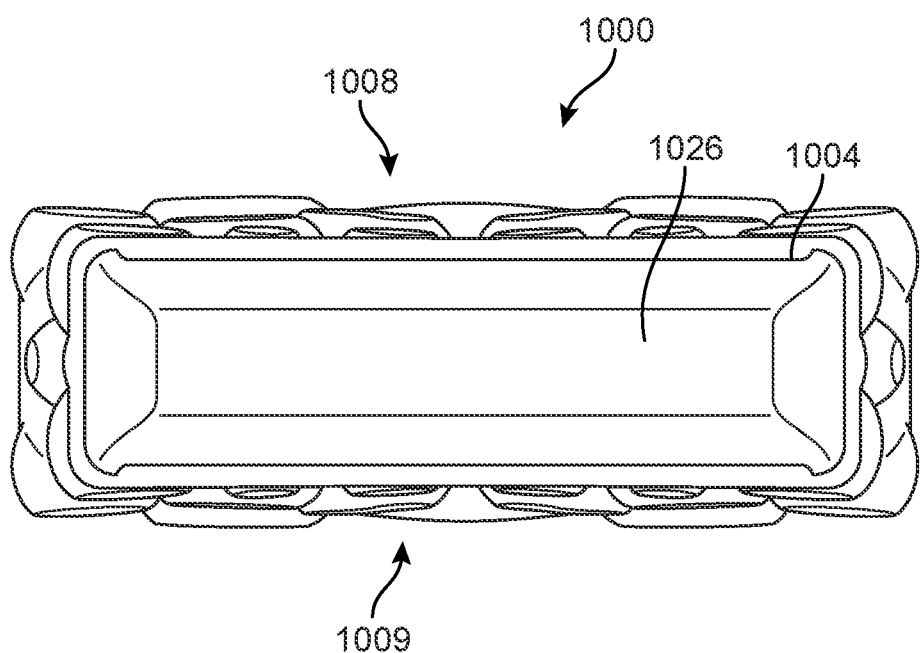
FIG. 16 is a posterior view of the implant of FIG. 15.

FIG. 14 is a schematic isometric view of an embodiment of an implant 800 including a plurality of bone contacting elements 802. Implant 800 is configured with surface texturing 804, which is depicted using stippling. In some embodiments, some portions of implant 800 could have surface texturing. In other embodiments, all portions of implant 800 could have surface texturing. In the embodiment depicted in FIG. 14, surface texturing 804 is applied throughout a majority of implant 800. However, at least some portions do not include surface texturing, including posterior surface 806 of posterior body member 808. This may help prevent bone growth from developing towards the spinal column. In some cases, an anterior surface (not shown) may also lack surface texturing.

Additional Embodiments

Embodiments can include provisions for modifying the strength of an implant in one or more directions to better withstand various loading, such as vertical loading applied by adjacent vertebrae. In some embodiments, the shape and/or size of one or more bone contacting elements can be modified to vary the strength of the implant at one or more sides and/or along one or more directions. In other embodiments, additional support structures can be incorporated into an implant to reinforce one or more sides. In some cases, for example, embodiments could incorporate one or more support walls, for example, on the lateral sides of an implant, which may intersect one or more bone contacting elements.

FIGS. 15-20 illustrate schematic views of another embodiment of an implant 1000. Referring first to FIGS. 15-18, implant 1000 may be configured with similar provisions to implant 100. For example, implant 1000 may generally include a first body member 1002 and second body member 1004 that are connected by various bone contacting elements 1010. First body member 1002 may comprise a generally smooth and flat anterior face 1020, which further includes a recessed region 1022 and threaded opening 1024. Furthermore, second body member 1004 is seen to have a generally smooth and flat posterior face 1026.

Figure 17:
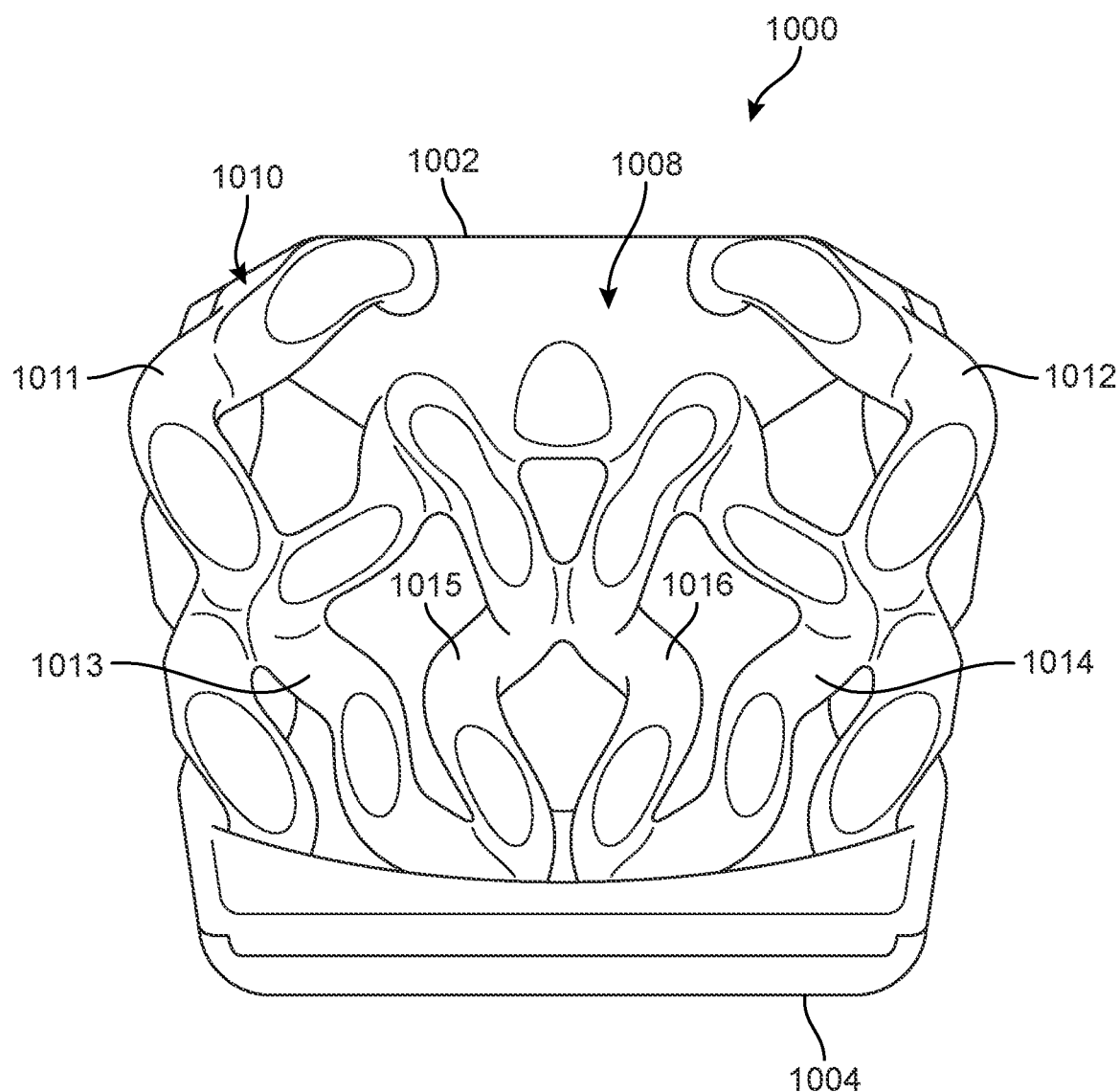
FIG. 17 is a superior view of the implant of FIG. 15.

Implant 1000 also comprises generally helical bone contacting elements arranged on superior side 1008 (see FIGS. 15-16) and the opposing inferior side 1009. On superior side 1008, as best seen in FIG. 17, bone contacting elements 1010 includes a first bone contacting element 1011, a second bone contacting element 1012, a third bone contacting element 1013, a fourth bone contacting element 1014, a fifth bone contacting element 1015 and a sixth bone contacting element 1016, which may be arranged in an approximately similar manner to first bone contacting element 411, second bone contacting element 421, third bone contacting element 431, fourth bone contacting element 441, fifth bone contacting element 451 and sixth bone contacting element 461, respectively, of implant 100. This similar configuration includes, for example, locations where adjacent bone contacting elements connect in a tangential way (i.e., along their respective sidewalls). It may be appreciated that in some embodiments inferior side 1009 can include a mirror symmetric arrangement of bone contacting elements from those on superior side 1008.

In some embodiments, implant 1000 can include provisions that increase vertical strength or support for the device. Referring now to the lateral side view shown in FIG. 18, a support wall 1050 may be disposed in the region between first bone contacting element 1011 on superior side 1008 and a second bone contacting element 1061 on inferior side 1009.

Figure 18:
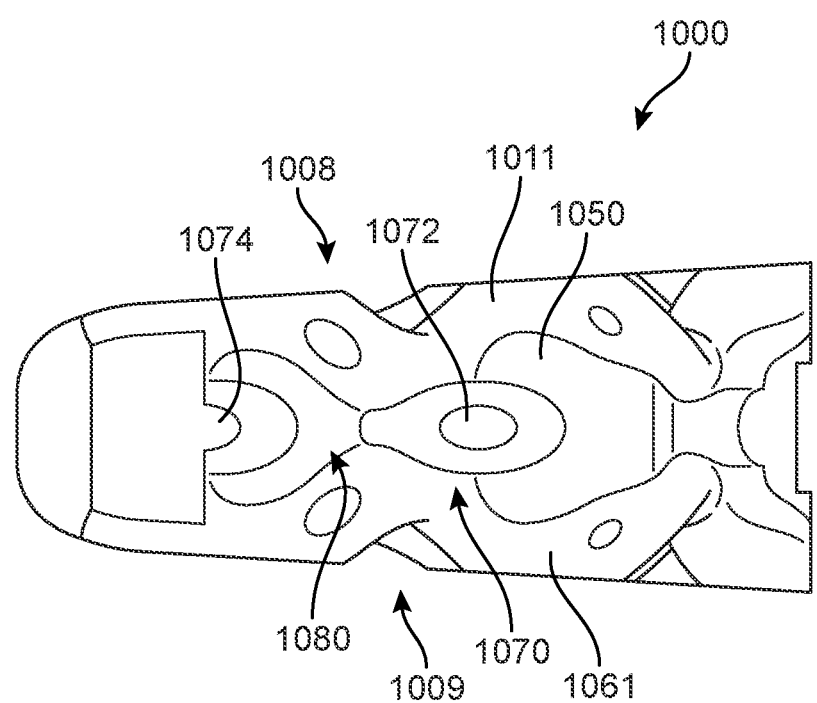
FIG. 18 is a lateral view of the implant of FIG. 15.

In some embodiments, a support wall may be used with an undulating planar bone contacting element to increase vertical strength. In FIG. 18, implant 1000 is seen to include an undulating planar bone contacting element 1070 that extends along the transverse plane and provides support to bone contacting element 1011 and second bone contacting element 1061. Moreover, undulating planar bone contacting element 1070 is seen to intersect with support wall 1050.

Figure 19:
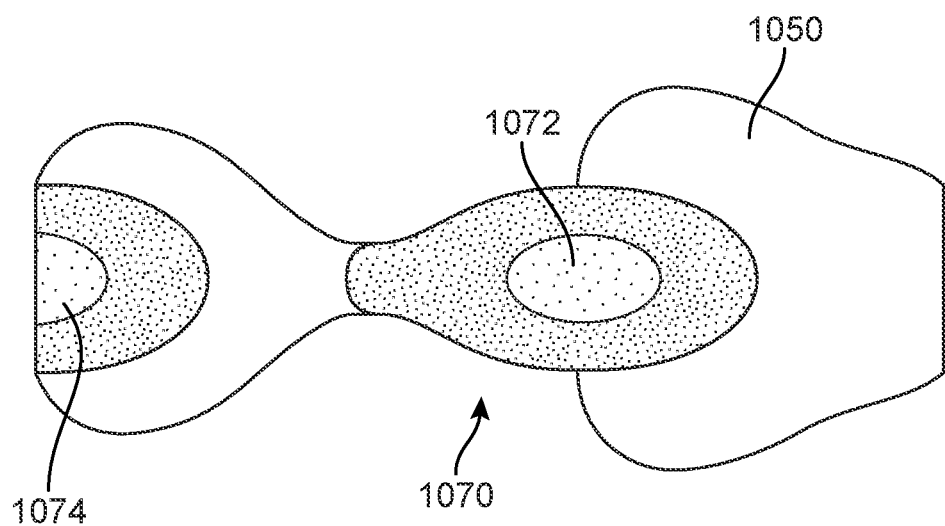
FIG. 19 is a schematic view of a bone contacting element intersecting a support wall according to an embodiment.
Figure 20:
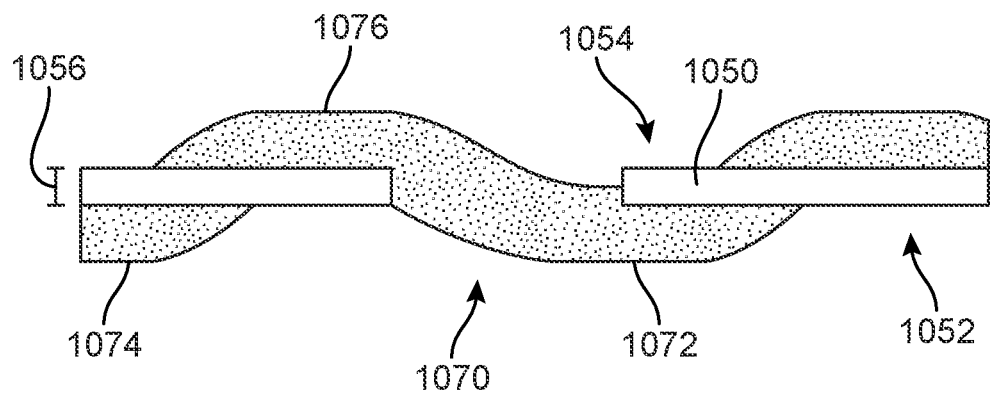
FIG. 20 is a top down view of the bone contacting element intersecting the support wall of FIG. 19.

FIGS. 19 and 20 are schematic views of support wall 1050 and an undulating planar bone contacting element 1070 that extends from opposing surfaces of support wall 1050. Referring to FIGS. 19-20, undulating planar bone contacting element 1070 is integral with support wall 1050. A first bone contacting region 1072 and a second bone contacting region 1074 extend out from an exterior side 1052 of support wall 1050. Likewise, a proximal region 1076 of undulating planar bone contacting element 1070 extends out from an interior side 1054 of support wall 1050.

In different embodiments, the properties of a support wall could be selected to achieve a desired degree of vertical strength on the lateral side of a device. In some embodiments, a support wall may extend through any otherwise open spacing between opposing helical bone contacting elements on a lateral side of an implant. In other embodiments, a support wall could only partially extend between opposing helical bone contacting elements, thus leaving openings or other gaps in a lateral side of an implant. In some embodiments, the thickness of a support wall could be greater than the diameter of the opposing helical elements. In other embodiments, the thickness of a support wall could be less than the diameter of opposing helical elements. For example, it may be clearly seen in FIGS. 19-20 that the thickness 1056 of support wall 1050 may be less than the diameter of generally helical first bone contacting element 1011.

Using this arrangement, a lateral side of implant 1000 may be provided with additional vertical support from support wall 1050 while maintaining at least one region 1080 for protecting new bone growth (see FIG. 18). Specifically, region 1080 is seen to be recessed from bone first bone contacting region 1072 and second bone contacting region 1074.

FIGS. 21-25 illustrate schematic views of another embodiment of an implant 1200. Referring first to FIGS. 21-24, implant 1200 may be configured with similar provisions to implant 100 and/or implant 1000. For example, implant 1200 may generally include a first body member 1202 and second body member 1204 that are connected by various bone contacting elements 1210. First body member 1202 may comprise a generally smooth and flat anterior face 1220, which further includes a recessed region 1222 and threaded opening 1224. Furthermore, second body member 1204 is seen to have a generally smooth and flat posterior face 1226.

Figure 21:
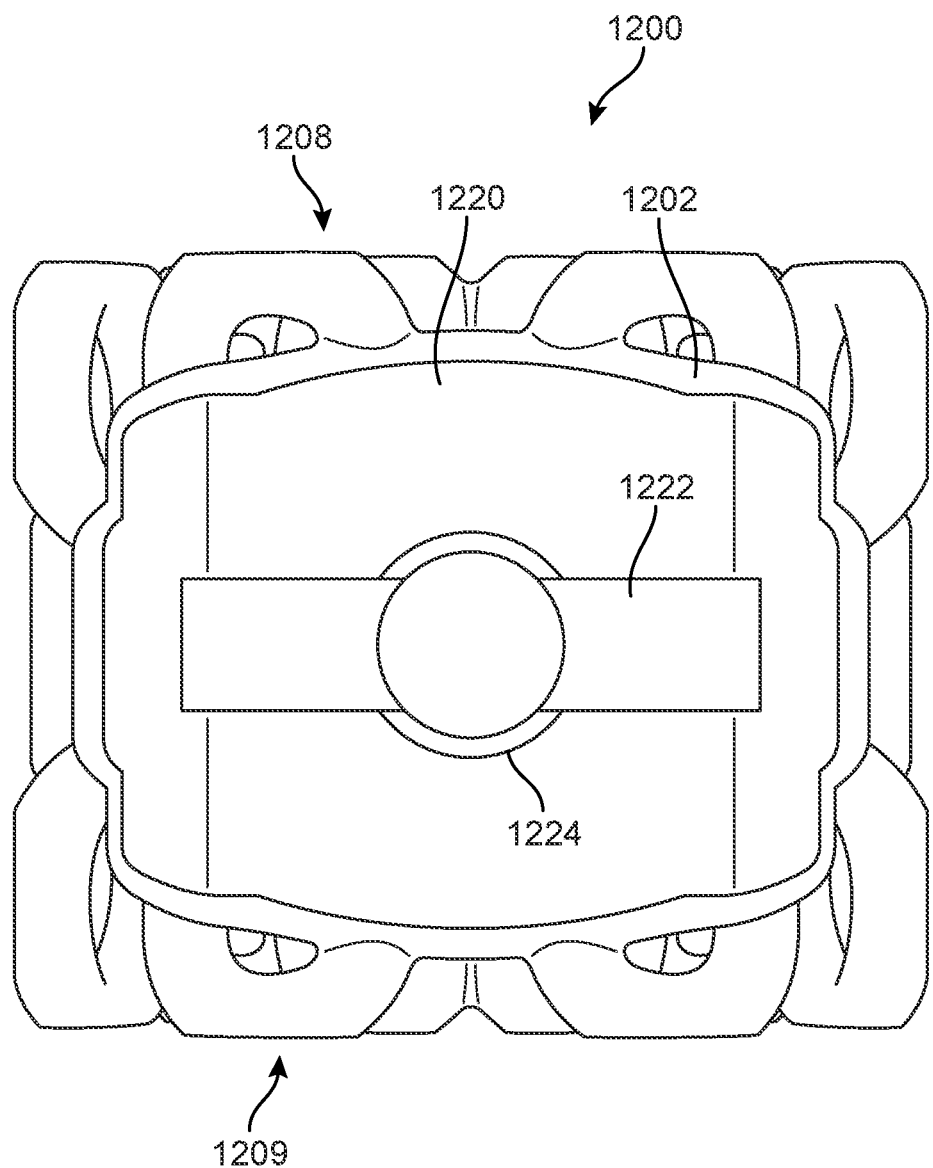
FIG. 21 is an anterior view of another embodiment of an implant with bone contacting elements.
Figure 22:
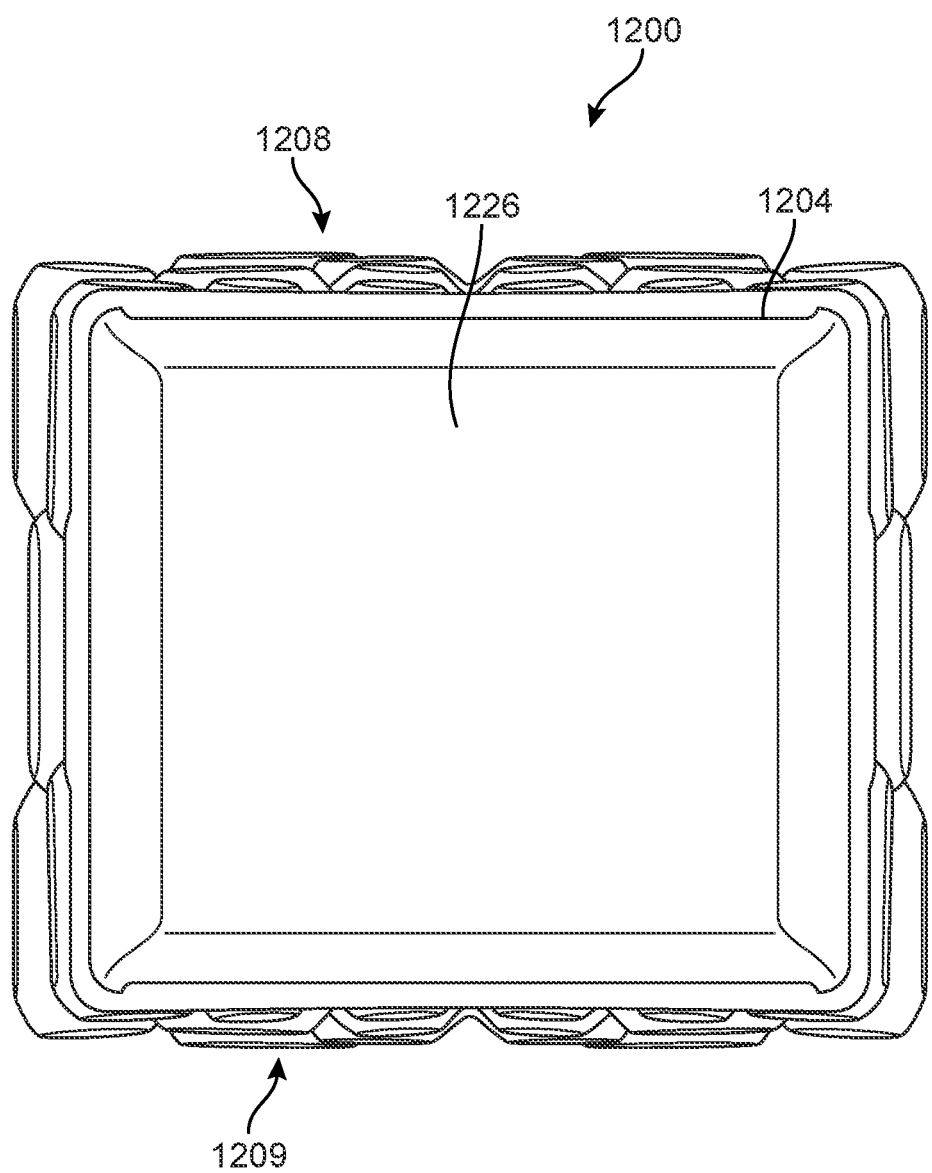
FIG. 22 is a posterior view of the implant of FIG. 21.
Figure 23:
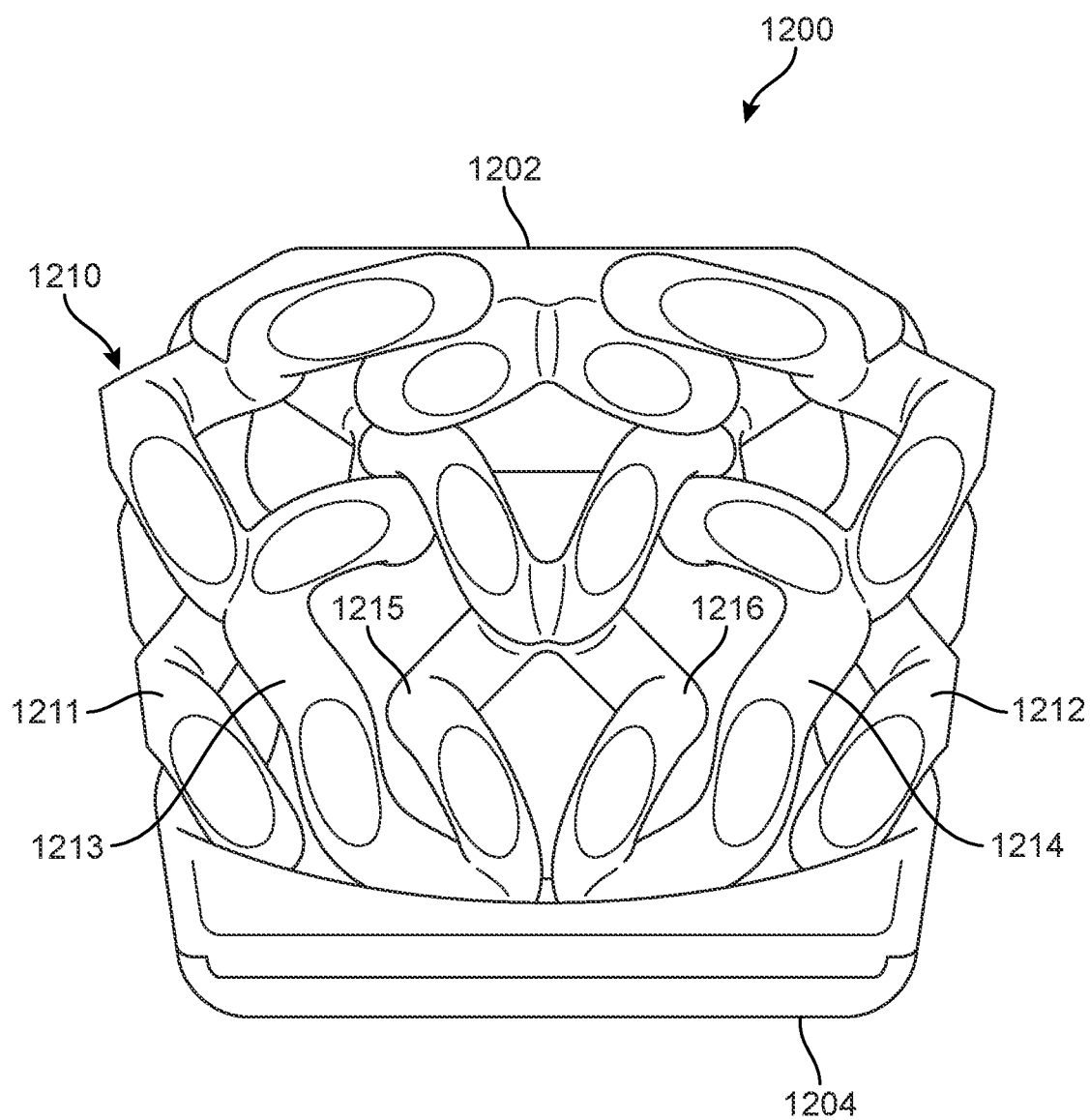
FIG. 23 is a superior view of the implant of FIG. 21.

Implant 1200 also comprises generally helical bone contacting elements arranged on superior side 1208 and the opposing inferior side 1209 (see FIGS. 21-22). On superior side 1208, bone contacting elements 1210 includes a first bone contacting element 1211, a second bone contacting element 1212, a third bone contacting element 1213, a fourth bone contacting element 1214, a fifth bone contacting element 1215 and a sixth bone contacting element 1216, which may be arranged in an approximately similar manner to first bone contacting element 411, second bone contacting element 421, third bone contacting element 431, fourth bone contacting element 441, fifth bone contacting element 451 and sixth bone contacting element 461, respectively, of implant 100. This similar configuration includes, for example, locations where adjacent bone contacting elements connect in a tangential way (i.e., along their respective sidewalls). It may be appreciated that in some embodiments inferior side 1209 can include a mirror symmetric arrangement of bone contacting elements from those on superior side 1208.

In some embodiments, the geometry of a bone contacting element may be selected to achieve a desired degree of vertical strength for a device. In some embodiments, a bone contacting element may have a cross-sectional shape that is elongated in a dimension aligned with the vertical direction (e.g., the height of the element) relative to a dimension aligned with the lateral direction (e.g., the thickness of the element). In some embodiments, the cross-sectional shape could be approximately elliptic. In other embodiments, the cross-sectional shape could be approximately rectangular.

As seen in FIG. 24, implant 1200 includes bone contacting element 1260, which has a non-circular cross-sectional shape. In one embodiment, bone contacting element 1260 has a rectangular cross-sectional shape 1320. This is best shown in FIG. 25, which illustrates a schematic view of bone contacting element 1260 in isolation from implant 1200. As seen in FIG. 25, bone contacting element 1260 includes a height 1302 that is greater than its width 1304. By increasing the height of bone contacting element 1260 relative to the size (e.g., diameter) of adjacent bone contacting elements (i.e., helical bone contacting element 1271 and helical bone contacting element 1272), the overall strength of implant 1200 under vertical loading may be increased.

Bone contacting element 1260 also has an undulating geometry. As best seen in FIG. 25, an exterior surface curve 1310 of bone contacting element 1260 is seen to be an undulating planar curve. Here, exterior surface curve 1310 may be defined by the intersection of a plane with exterior surface 1360 of bone contacting element 1260. It may be appreciated that while the exemplary embodiment depicts bone contacting element 1260 as having an undulating interior surface 1362 that matches the curvature of exterior surface 1360, in other embodiments interior surface 1362 could be relatively flat.

The undulating configuration depicted in FIGS. 24-25 ensures that bone contacting element 1260 presents bone contacting regions 1266 on the lateral side of implant 1200 as well as provides protected fusion zones 1268 located in the locations between the bone contacting regions 1266.

Different embodiments could vary in size. In some embodiments, the "footprint" of an implant could vary. As used herein, the footprint of the device comprises its approximate area in the transverse (or another horizontal) plane. In some embodiments, an implant could be manufactured in two or more distinct footprint sizes. In some embodiments, an implant could be manufactured in three or more distinct footprint sizes, including a small, medium and large footprint. Implants of different footprint sizes could be used to accommodate different sized vertebrae. In one embodiment, footprint sizes may be as follows: a small footprint having dimensions of 12×14.5 mm; a medium footprint having dimensions of 12.5×16 mm; and a large footprint having dimensions of 13×18 mm.

Different embodiments could incorporate implants of varying heights. For example, an implant could be manufactured in two or more distinct heights. In other embodiments, an implant could be manufactured in three or more distinct heights. In some embodiments, implants could be manufactured in any heights in a range between approximately 5 and 12 mm. In some embodiments, an implant could be manufactured in a 5 mm height, an 8 mm height and a 12 mm height. An embodiment of a 5 mm height device is depicted in FIGS. 15-20. An embodiment of a 12 mm height device is depicted in FIGS. 21-25.

Embodiments can also be provided with various flat/parallel (0-degree), lordotic, and hyper-lordotic angles. In some embodiments, the implant can be configured with an approximately 8-degree angle between the superior and inferior surfaces. In other embodiments, the implant can be configured with an approximately 15-degree angle between the superior and inferior surfaces. In still other embodiments, the implant can be configured with an approximately 20-degree angle between the superior and inferior surfaces. Still other angles are possibly including any angles in the range between 0 and 30 degrees. Still other embodiments can provide a lordotic angle of less than 8 degrees. Still other embodiments can provide a hyper-lordotic angle of more than 20 degrees.

In different embodiments, one or more sides of an implant could be configured with a predetermined curvature. In some embodiments, a superior and/or inferior surface could be configured with a convex geometry that engages the concave geometry of the opposing vertebral surfaces. In other embodiments, however, the inferior and/or superior surfaces of an implant could be concave, flat, tapered/angulated to provide lordosis or kyphosis, etc. in shape.

FIGS. 26-36 illustrate various views of additional embodiments of implants that may incorporate bone contacting elements having generalized helical geometries and bone contacting elements having undulating planar geometries. These embodiments are representative of implants that may be configured with different footprint dimensions and/or heights. For example, the embodiment depicted in FIGS. 26-29 may correspond with an implant having a large footprint (approximately 13×18 mm) and height of approximately 8 mm. Likewise, the embodiment depicted in FIG. 30 may correspond with an implant having a large footprint and a height of approximately 10-12 mm. Furthermore, the embodiment depicted in FIGS. 31-33 may correspond with an implant having a small footprint (approximately 12×14.5 mm) and a height of approximately 10-12 mm. The embodiment depicted in FIGS. 34-36 may correspond with an implant having a small footprint and a height of approximately 5-6 mm.

Figure 26:
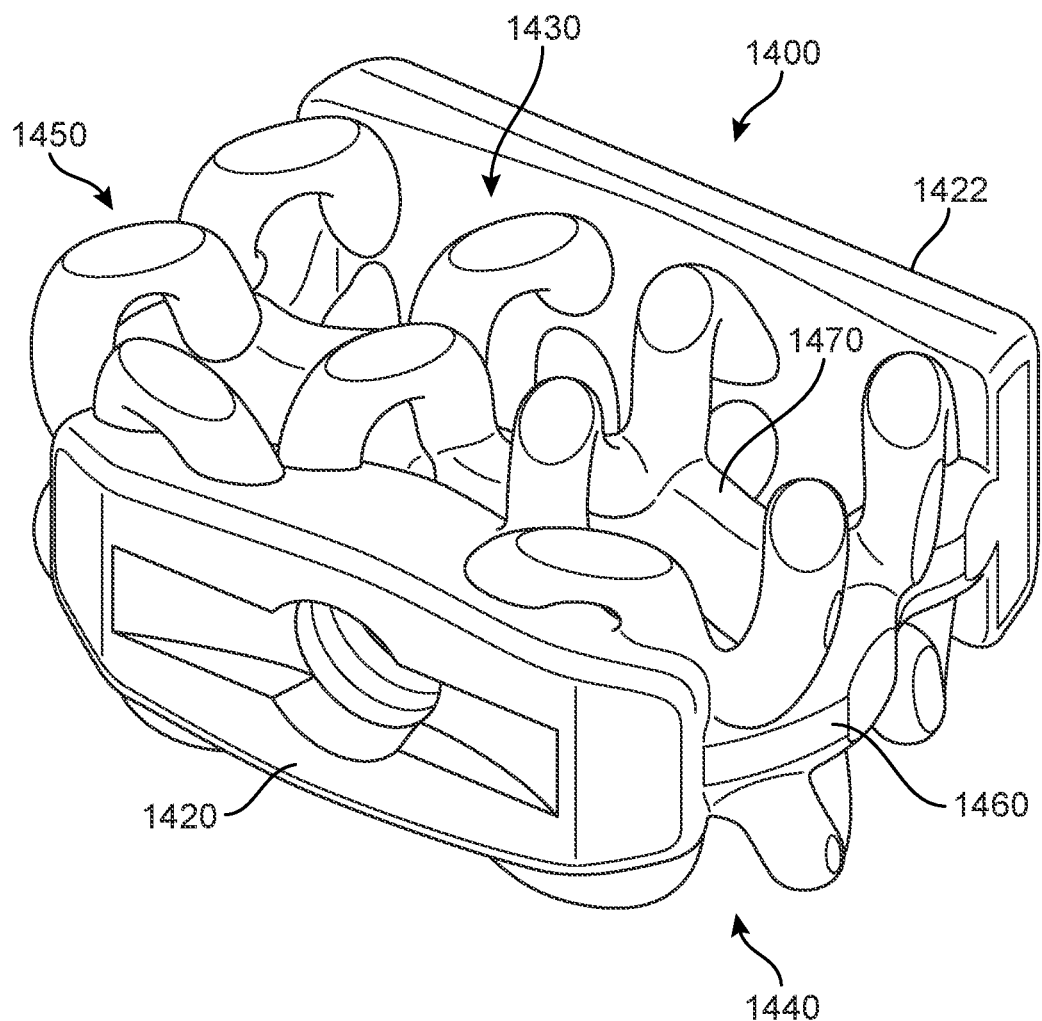
FIG. 26 is an isometric view of an embodiment of an implant.
Figure 27:
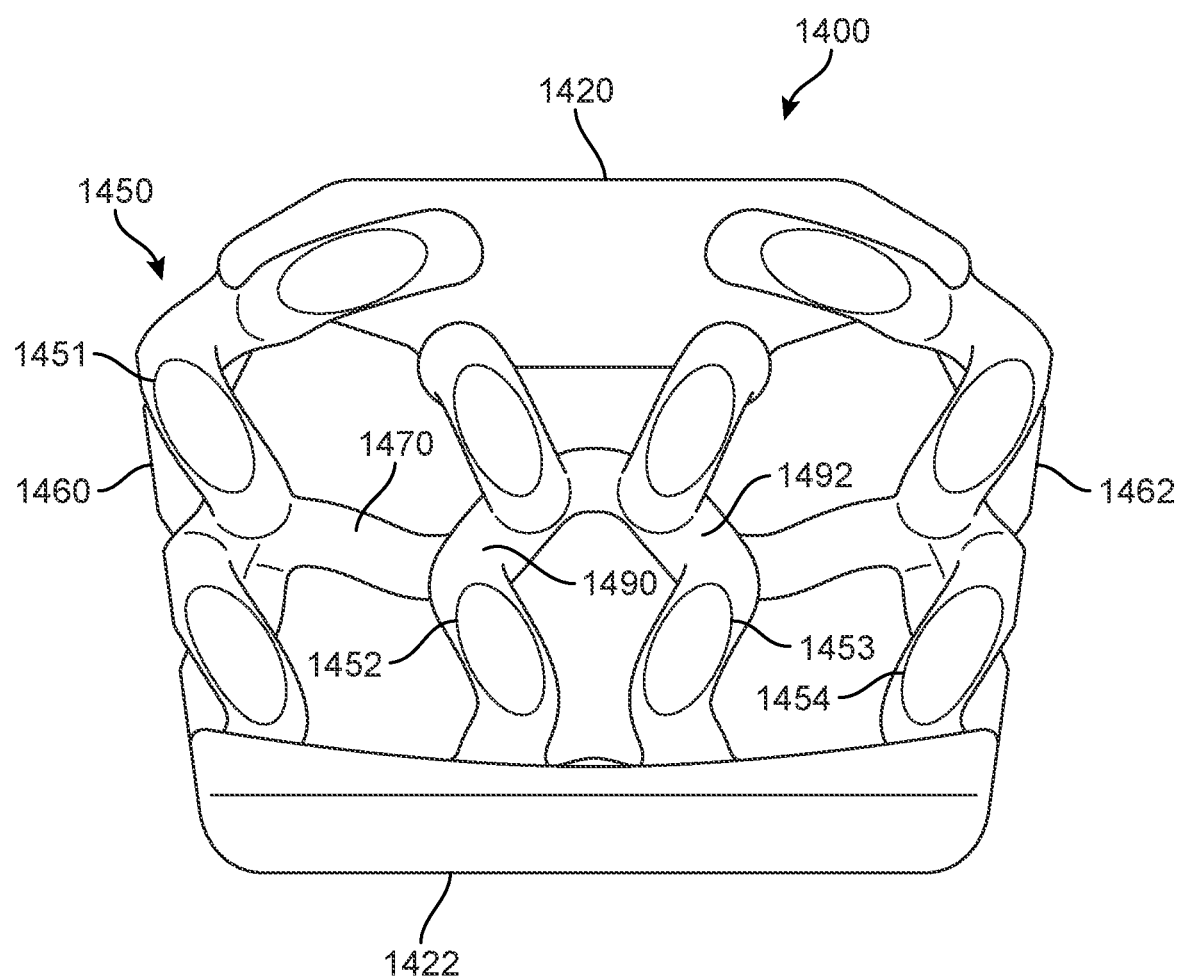
FIG. 27 is a superior view of the implant of FIG. 26.
Figure 28:
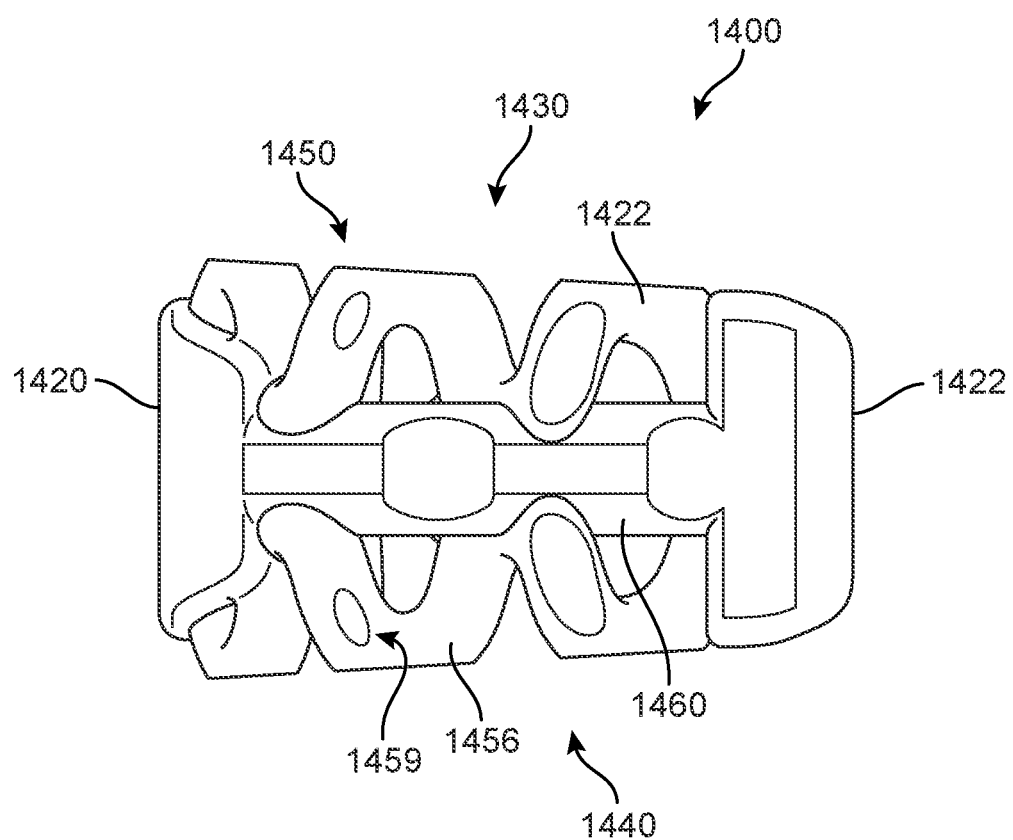
FIG. 28 is a lateral view of the implant of FIG. 26.

FIGS. 26-29 illustrate various schematic views of an embodiment of an implant 1400. Implant 1400 may share similar provisions with one or more of the previous embodiments of FIGS. 1-25. Referring to FIGS. 26-28, in some embodiments, implant 1400 includes a first body member 1420 and a second body member 1422. Additionally, a set of bone contacting elements 1450 having a generally helical geometry may extend from first body member 1420 to second body member 1422 on superior side 1430 and inferior side 1440. Furthermore, implant 1400 may include a first peripheral bone contacting element 1460 and a second peripheral bone contacting element 1462 on the lateral sides of implant 1400, each of these elements having an undulating planar geometry.

As seen in FIG. 27, set of bone contacting elements 1450 may include four generalized helical elements on superior side 1430. These include a first superior bone contacting element 1451, a second superior bone contacting element 1452, a third superior bone contacting element 1453 and a fourth superior bone contacting element 1454, which each extend from first body member 1420 to second body member 1422.

Embodiments may include provisions to enhance strength along a lateral direction of an implant. In some embodiments, an implant could include one or more straight struts or beams arranged in a generally lateral direction across portions of an implant. In other embodiments, an implant could include one or more curved bone contacting elements arranged along a lateral direction of an implant. In some cases, a laterally arranged bone contacting element could have a generalized helical geometry. In other cases, a laterally arranged bone contacting element could have an undulating planar geometry.

As seen in FIGS. 26 and 27, implant 1400 may include a central bone contacting element 1470 that generally extends between opposing lateral sides of implant 1400 (and therefore between first peripheral bone contacting element 1460 and second peripheral bone contacting element 1462). As seen in FIG. 27, as well as in FIG. 29 (which shows implant 1400 with set of bone contacting elements 1450 removed), central bone contacting element 1470 has an undulating planar geometry.

In some embodiments, one or more adjacent bone contacting elements may have portions that align with, or are oriented along, a section of central bone contacting element 1470. As best seen in FIG. 27, second superior bone contacting element 1452 has a central portion 1490 that is aligned (or parallel) with the adjacent portion of central bone contacting element 1470. Likewise, third superior bone contacting element 1453 may include a central portion 1492 that is aligned (or parallel) with the adjacent portion of central bone contacting element 1470. This arrangement may improve strength by increasing the area to which each generalized helical element is attached to central bone contacting element 1470.

Figure 29:
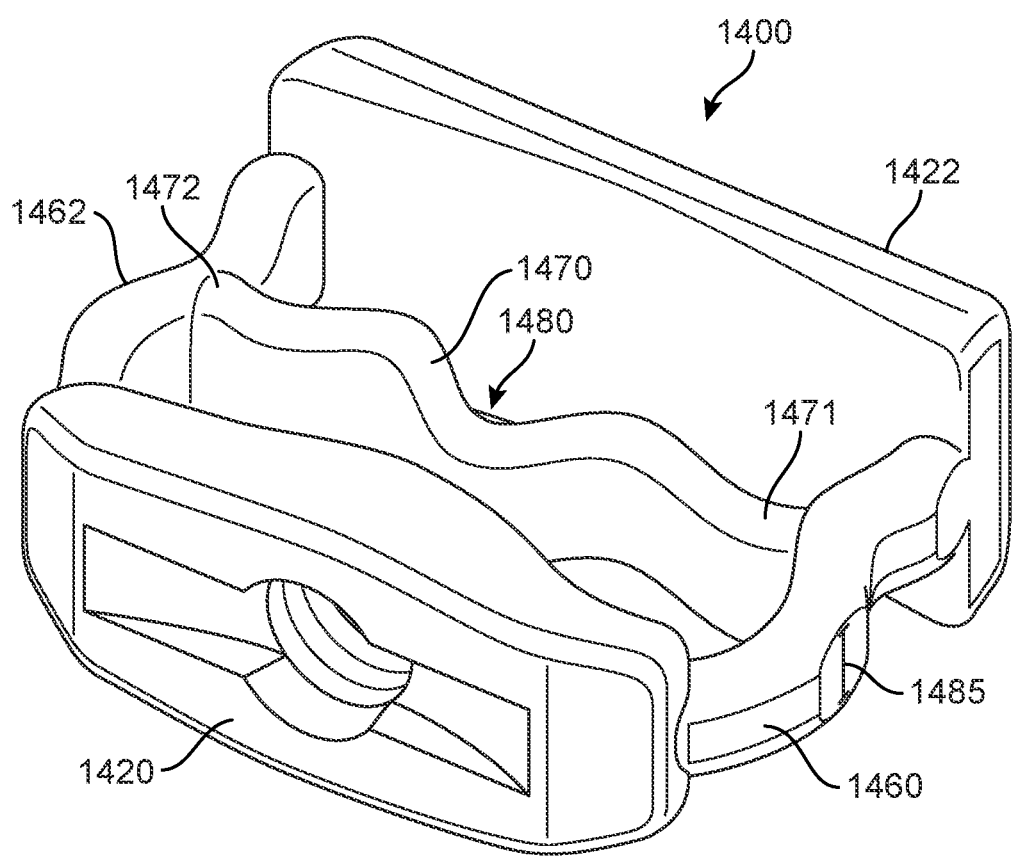
FIG. 29 is an isometric view of the implant of FIG. 26, in which some bone contacting elements have been removed for clarity.

Moreover, as seen in FIG. 29, first peripheral bone contacting element 1460, second peripheral bone contacting element 1462 and central bone contacting element 1470 may all be aligned in a common plane, such as the transverse plane of implant 1400. Specifically, a first end 1471 of bone contacting element 1470 attaches to a portion of first bone contacting element 1460 and a second end 1472 of central bone contacting element 1470 attaches to a portion of second bone contacting element 1462.

This configuration may help to strengthen implant 1400 in the lateral direction while also promoting bone growth within the interior of implant 1400. For example, the undulating planar geometry of central bone contacting element 1470 may create protected fusion zones 1480 between adjacent crests of the element, helping to minimize disturbances of new bone growth within these zones.

Figure 30:
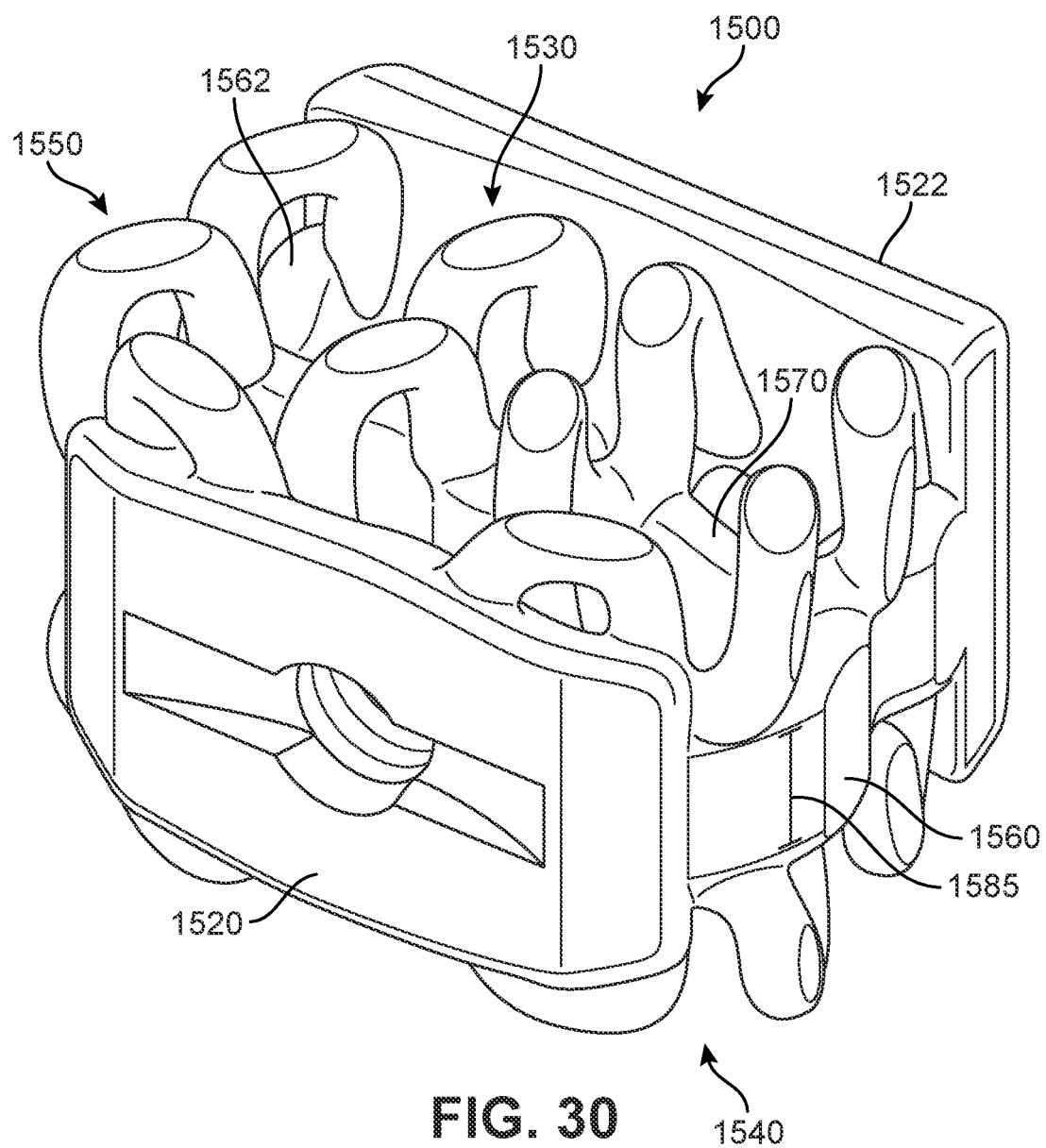
FIG. 30 is an isometric view of another embodiment of an implant.

FIG. 30 is a schematic isometric view of another embodiment of an implant 1500. Implant 1500 may share many provisions with implant 1400. In some embodiments, implant 1500 includes a first body member 1520 and a second body member 1522. Additionally, a set of bone contacting elements 1550 having a generally helical geometry may extend from first body member 1520 to second body member 1522 on superior side 1530 and inferior side 1540. Furthermore, implant 1500 may include a first peripheral bone contacting element 1560 and a second peripheral bone contacting element 1562 on the lateral sides of implant 1500, each of these elements having an undulating planar geometry. Additionally, implant 1500 may include a central bone contacting element 1570 with an undulating planar geometry that extends laterally across implant 1500.

However, implant 1500 may be configured with a greater height than implant 1400. To achieve a greater height, the height of the generally helical elements and/or undulating planar elements could be increased relative to their heights in, for example, implant 1400. In the exemplary embodiment, peripheral bone contacting element 1560 has a height 1585 that may be greater than a height 1485 of peripheral bone contacting element 1460 of implant 1400 (see FIG. 29). Moreover, the height 1585 of bone contacting element 1560 relative to its width may be greater than the height 1485 of element 1460 relative to its width. Thus, it may be appreciated that the general dimensions of undulating planar elements can be varied to achieve different strength characteristics.

Figure 31:
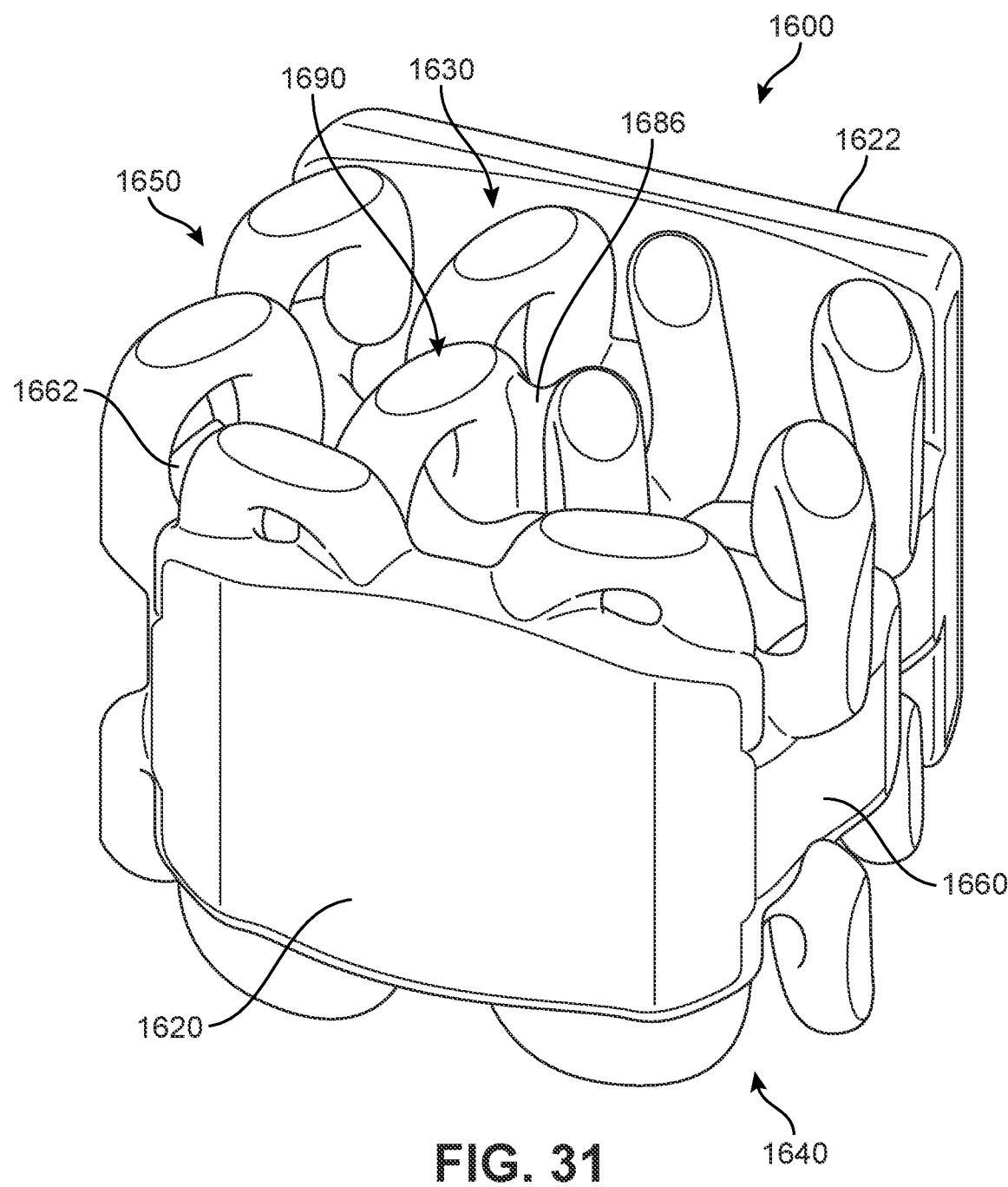
FIG. 31 is an isometric view of another embodiment of an implant.
Figure 32:
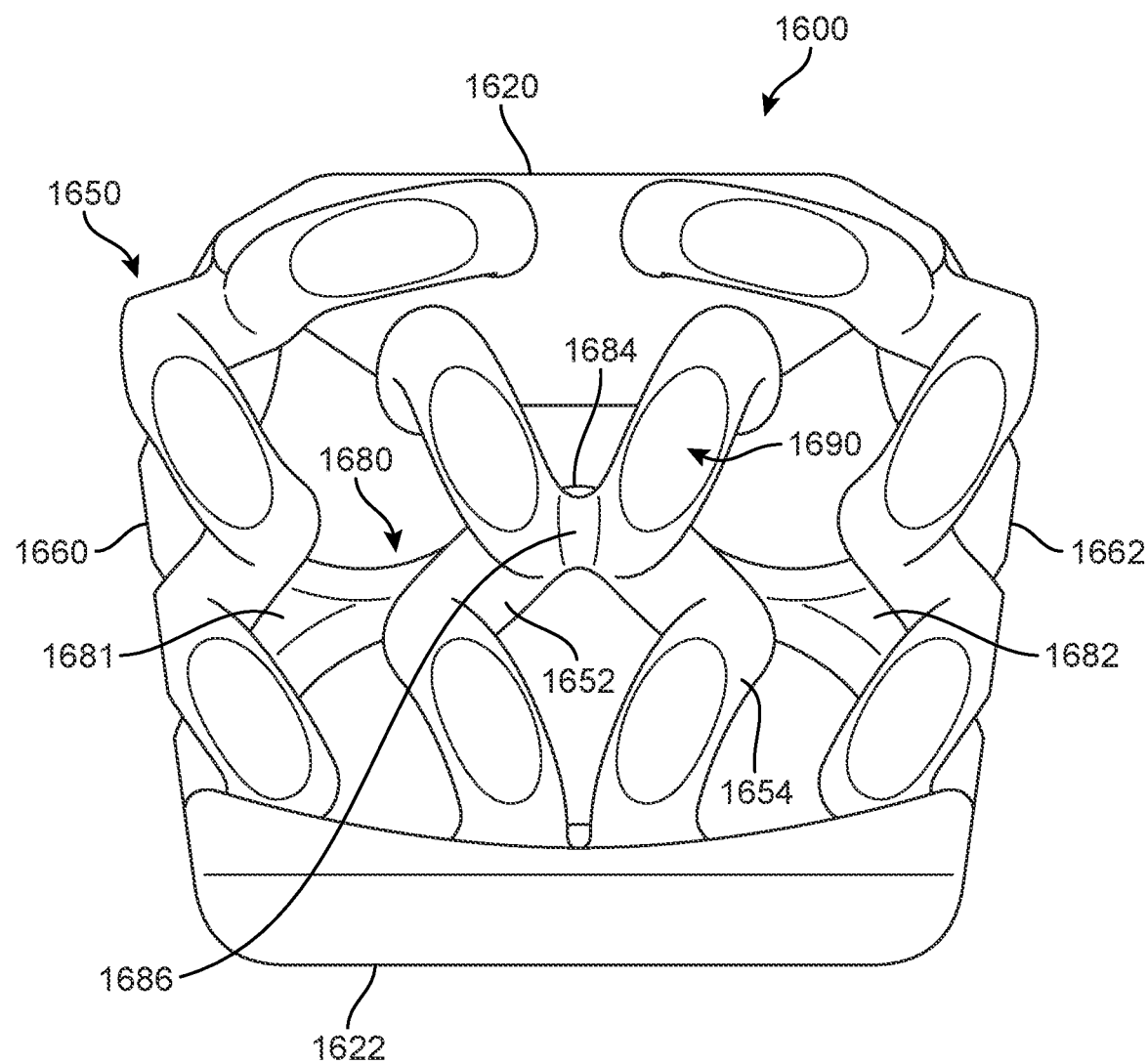
FIG. 32 is a superior view of the implant of FIG. 31.
Figure 33:
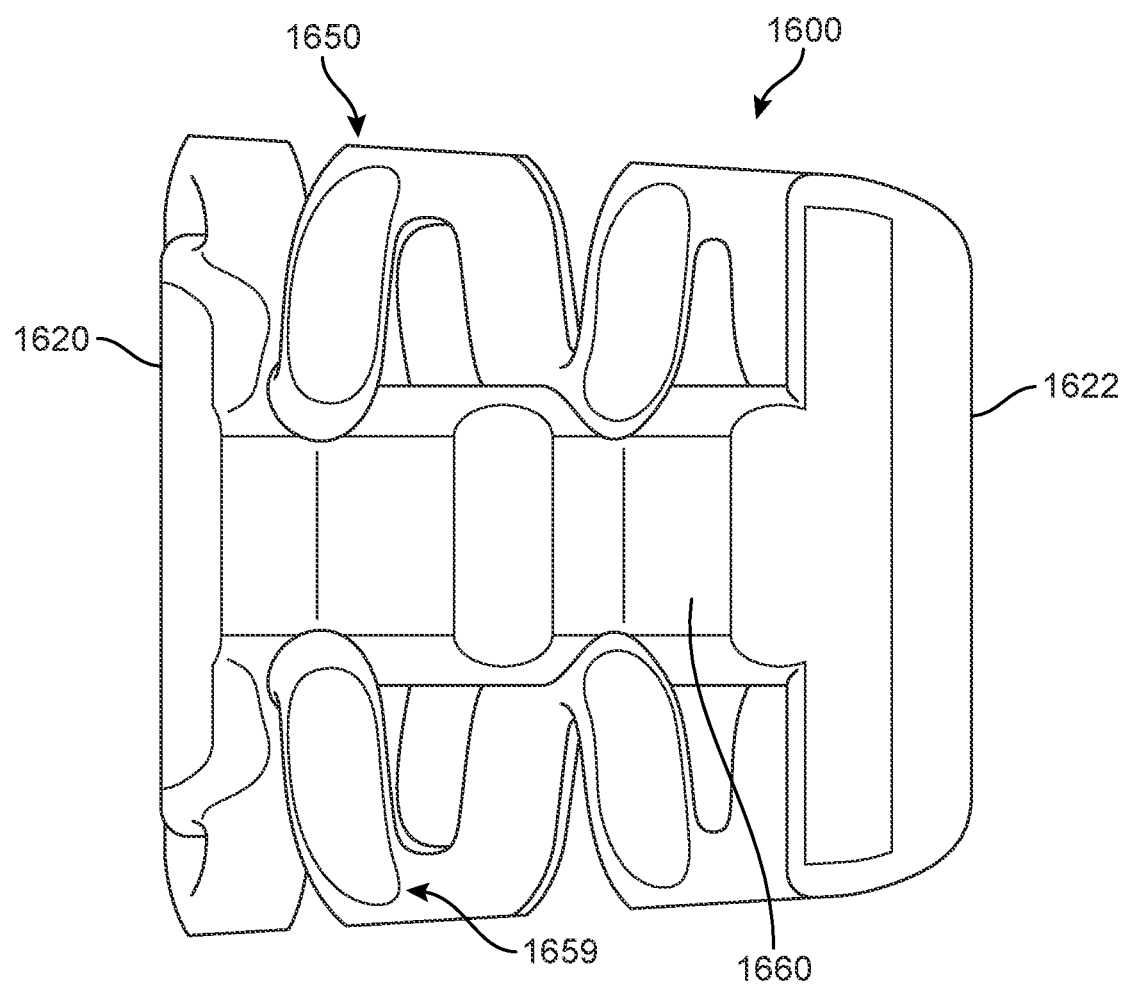
FIG. 33 is a lateral view of the implant of FIG. 31.

In different embodiments, the geometry and/or arrangement of one or more elements could be modified to vary the lateral strength. FIGS. 31-33 illustrate several schematic views of an implant 1600. Implant 1600 may share many provisions with implant 1400 and/or implant 1500. In some embodiments, implant 1600 includes a first body member 1620 and a second body member 1622. Additionally, a set of bone contacting elements 1650 having a generally helical geometry may extend from first body member 1620 to second body member 1622 on superior side 1630 and inferior side 1640. Furthermore, implant 1600 may include a first peripheral bone contacting element 1660 and a second peripheral bone contacting element 1662 on the lateral sides of implant 1600, each of these elements having an undulating planar geometry.

In contrast to implant 1400, implant 1600 may include a lateral support element 1680 that has a different geometry from bone contacting element 1470. For example, lateral support element 1680 may be widest (with respect to the longitudinal direction) at its lateral most ends (i.e., end 1681 and end 1682). The width of lateral support element 1680 may taper at the lateral ends to a central portion 1684, which attaches to a bone contacting element 1652 and a bone contacting element 1654 of set of bone contacting elements 1650.

In order to further enhance lateral support, in some embodiments, superior bone contacting element 1652 and superior bone contacting element 1654 may be attached along a connecting portion 1686 that extends all the way from lateral support element 1680 up to a location directly adjacent the distally located bone contacting regions 1690.

Figure 34:
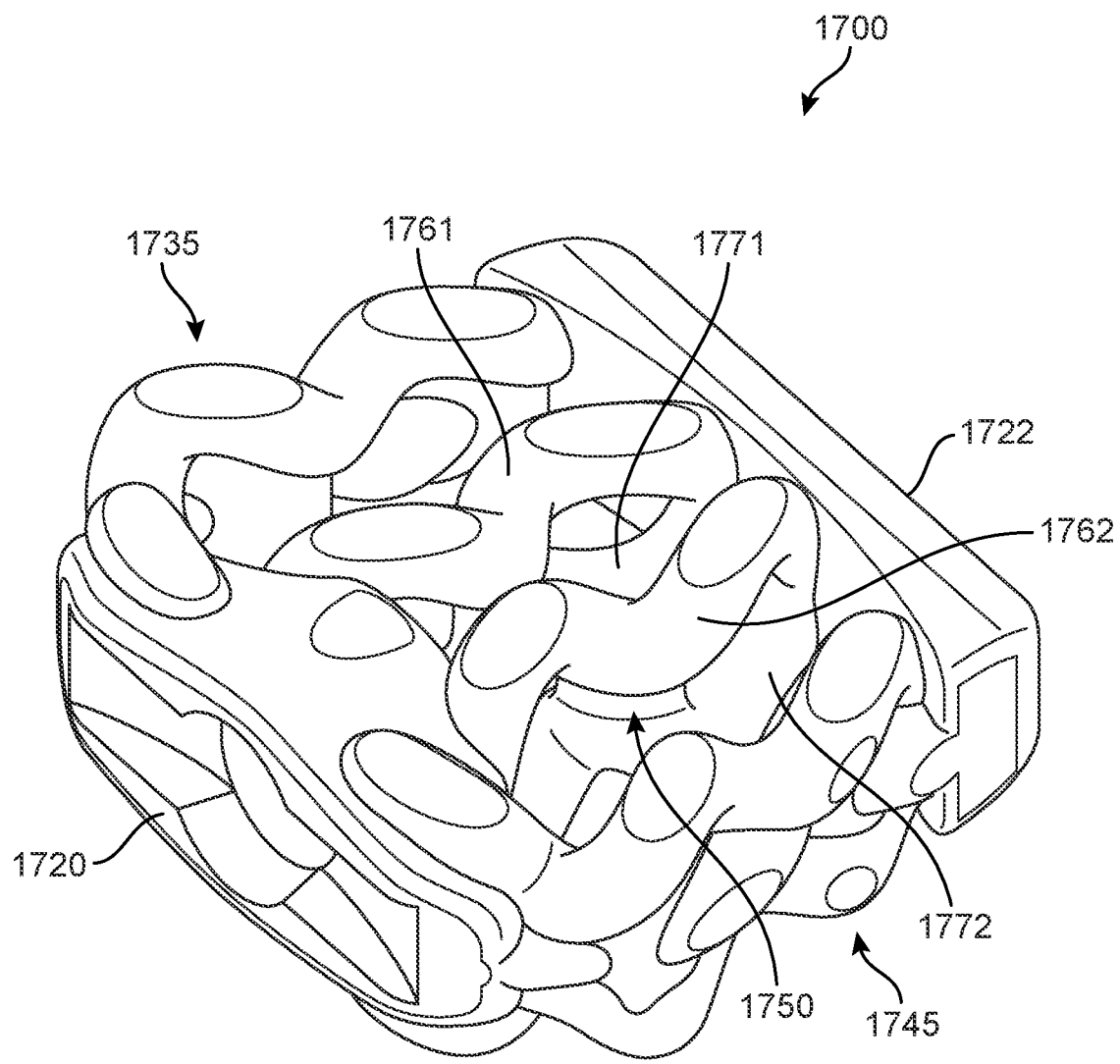
FIG. 34 is an isometric view of another embodiment of an implant.
Figure 35:
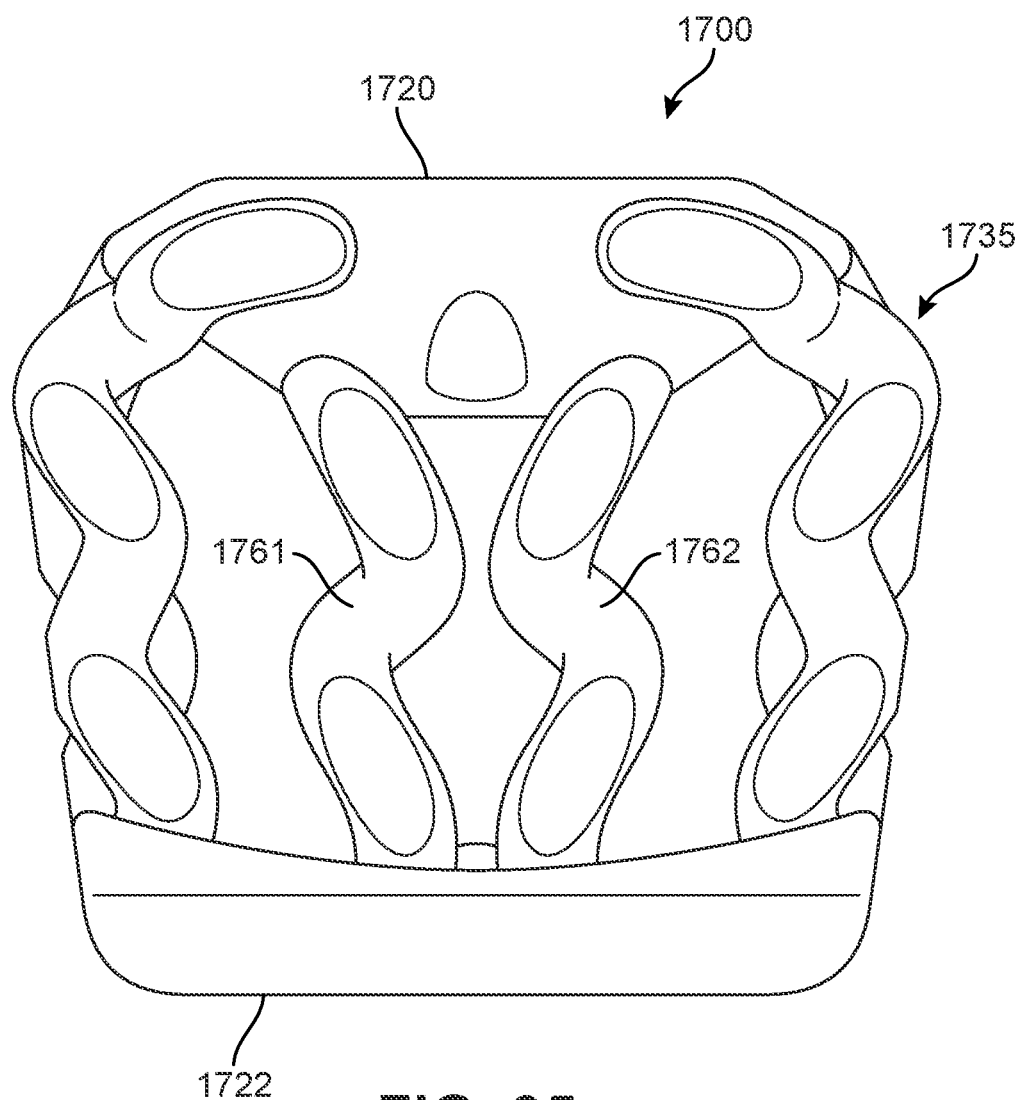
FIG. 35 is a superior view of the implant shown in FIG. 34.
Figure 36:
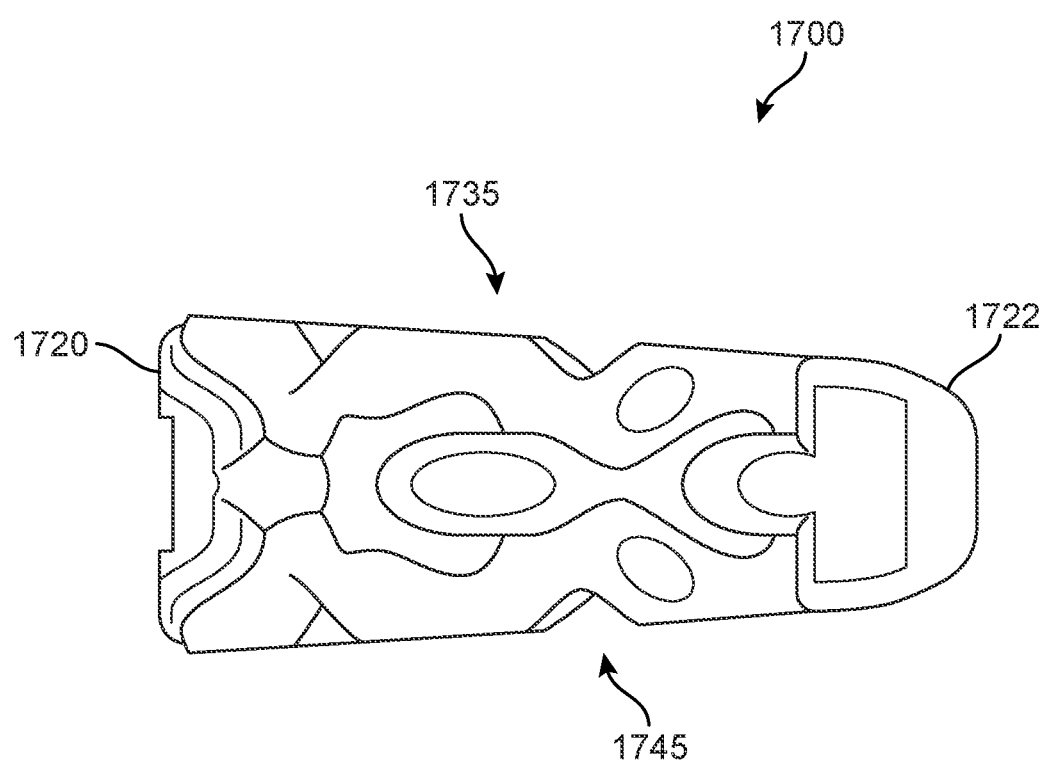
FIG. 36 is a lateral view of the implant shown in FIG. 34.

In yet another embodiment, shown in various schematic views in FIGS. 34-36, an implant 1700 is seen to lack any elements that extend laterally between the sides of implant 1700 (apart from first body member 1720 and second body member 1722). As seen in FIG. 34, a set of superior bone contacting elements 1735 may be directly attached to a set of inferior bone contacting elements 1745 adjacent a transverse plane of implant 1700. In some embodiments, pairs of corresponding elements from these two sets may be attached at central connecting portions 1750. In the embodiment of FIGS. 34-36, a first central superior bone contacting element 1761 is attached to a first central inferior bone contacting element 1771 and a second superior bone contacting element 1762 is attached to a second central inferior bone contacting element 1772.

In addition to variations in height, footprint and lateral support, the embodiments of FIGS. 26-36 all depict implants in which generally helical bone contacting elements on the superior and inferior sides of the implant each include on or more bone contacting regions. For example, as best seen in the lateral view of FIG. 28, superior bone contacting element 1451 and inferior bone contacting element 1456 both include two bone contacting regions 1459. Similarly, as best seen in the lateral side view of FIG. 33, implant 1600 also includes bone contacting regions 1659 on the laterally facing portions of bone contacting elements 1650. Along with the bone contacting regions disposed on undulating planar elements along the lateral sides of these implants, these additional bone contacting regions may help provide a consistent lateral engagement surface between the implants and bony tissue or other tissue following implantation.

Bone Growth Promoting Material

In some embodiments, bone growth can be facilitated by applying a bone growth promoting material in or around portions of an implant. As used herein, a "bone growth promoting material" (or BGPM) is any material that helps bone growth. Bone growth promoting materials may include provisions that are freeze dried onto a surface or adhered to the metal through the use of linker molecules or a binder. Examples of bone growth promoting materials are any materials including bone morphogenetic proteins (BMPs), such as BMP-1, BMP-2, BMP-4, BMP-6, and BMP-7. These are hormones that convert stem cells into bone forming cells. Further examples include recombinant human BMPs (rhBMPs), such as rhBMP-2, rhBMP-4, and rhBMP-7. Still further examples include platelet derived growth factor (PDGF), fibroblast growth factor (FGF), collagen, BMP mimetic peptides, as well as RGD peptides. Generally, combinations of these chemicals may also be used. These chemicals can be applied using a sponge, matrix or gel.

Some bone growth promoting materials may also be applied to an implantable prosthesis through the use of a plasma spray or electrochemical techniques. Examples of these materials include, but are not limited to, hydroxyapatite, beta tri-calcium phosphate, calcium sulfate, calcium carbonate, as well as other chemicals.

A bone growth promoting material can include, or may be used in combination with a bone graft or a bone graft substitute. A variety of materials may serve as bone grafts or bone graft substitutes, including autografts (harvested from the iliac crest of the patient's body), allografts, demineralized bone matrix, and various synthetic materials.

Some embodiments may use autograft. Autograft provides the spinal fusion with calcium collagen scaffolding for the new bone to grow on (osteoconduction). Additionally, autograft contains bone-growing cells, mesenchymal stem cells and osteoblast that regenerate bone. Lastly, autograft contains bone-growing proteins, including bone morphogenic proteins (BMPs), to foster new bone growth in the patient.

Bone graft substitutes may comprise synthetic materials including calcium phosphates or hydroxyapatites, stem cell containing products which combine stem cells with one of the other classes of bone graft substitutes, and growth factor containing matrices such as INFUSE® (rhBMP-2-containing bone graft) from Medtronic, Inc.

It should be understood that the provisions listed here are not meant to be an exhaustive list of possible bone growth promoting materials, bone grafts or bone graft substitutes.

In some embodiments, BGPM may be applied to one or more outer surfaces of an implant. In other embodiments, BGPM may be applied to internal volumes within an implant. In still other embodiments, BGPM may be applied to both external surfaces and internally within an implant.

Manufacturing and Materials

The various components of an implant may be fabricated from biocompatible materials suitable for implantation in a human body, including but not limited to, metals (e.g. titanium or other metals), synthetic polymers, ceramics, and/or their combinations, depending on the particular application and/or preference of a medical practitioner.

Generally, the implant can be formed from any suitable biocompatible, non-degradable material with sufficient strength. Typical materials include, but are not limited to, titanium, biocompatible titanium alloys (e.g. γTitanium Aluminides, $Ti_6$—$Al_4$—V ELI (ASTM F 136), or $Ti_6$—$Al_4$—V (ASTM F 1108 and ASTM F 1472)) and inert, biocompatible polymers, such as polyether ether ketone (PEEK) (e.g. PEEK-OPTIMA®, Invibio Inc). Optionally, the implant contains a radiopaque marker to facilitate visualization during imaging.

In different embodiments, processes for making an implant can vary. In some embodiments, the entire implant may be manufactured and assembled via injection-molding, cast or injection molding, insert-molding, co-extrusion, pultrusion, transfer molding, overmolding, compression molding, 3-Dimensional (3-D) printing, dip-coating, spray-coating, powder-coating, porous-coating, milling from a solid stock material and their combinations. Moreover, the embodiments can make use of any of the features, parts, assemblies, processes and/or methods disclosed in "The Coiled Implants Application."

While various embodiments have been described, the description is intended to be exemplary, rather than limiting and it will be apparent to those of ordinary skill in the art that many more embodiments and implementations are possible that are within the scope of the embodiments. Although many possible combinations of features are shown in the accompanying figures and discussed in this detailed description, many other combinations of the disclosed features are possible. Any feature of any embodiment may be used in combination with or substituted for any other feature or element in any other embodiment unless specifically restricted. Therefore, it will be understood that any of the features shown and/or discussed in the present disclosure may be implemented together in any suitable combination. Accordingly, the embodiments are not to be restricted except in light of the attached claims and their equivalents. Also, various modifications and changes may be made within the scope of the attached claims.

What is claimed is:

1. An implant, comprising:
a first body member and a second body member;
at least one bone contacting arched member extending between the first body member and the second body member; and
a first peripheral bone contacting element extending from the first body member to the second body member on a first lateral side of the implant;
a second peripheral bone contacting element extending from the first body member to the second body member on a second lateral side of the implant; and
a central bone contacting element that extends between the first peripheral bone contacting element and the second peripheral bone contacting element;
wherein the at least one bone contacting arched member bridges from the first body member to the central bone contacting element and bridges from the central bone contacting element to the second body member.

2. The implant according to claim 1, wherein the central bone contacting element has an undulating planar geometry.

3. The implant according to claim 2, wherein the central bone contacting element undulates in a substantially horizontal plane.

4. The implant according to claim 2, wherein the central bone contacting element having an undulating planar geometry has a substantially rectangular cross-sectional shape.

5. The implant according to claim 1, wherein the bone contacting arched member is a superior bone contacting element.

6. The implant according to claim 1, wherein the first body member is located on an anterior side of the implant, and wherein the second body member is located on a posterior side of the implant.

7. The implant according to claim 1, wherein a portion of the bone contacting arched member includes a portion that is aligned with a portion of the central bone contacting element.

8. The implant according to claim 7, further including a second bone contacting arched member;
wherein a portion of the second bone contacting arched member is aligned with a portion of the central bone contacting element.

9. The implant according to claim 7, wherein the bone contacting arched member is attached to the central bone contacting element in a region in which portions of the bone contacting arched member and the central bone contacting element are aligned.

10. The implant according to claim 1, wherein the central bone contacting element, the first peripheral bone contacting element, and the second peripheral bone contacting element are all aligned in a common plane.

11. The implant according to claim 10, wherein the central bone contacting element, the first peripheral bone contacting element, and the second peripheral bone contacting element are all aligned in a transverse plane of the implent.

12. An implant, comprising:
a first body member and a second body member;
at least one bone contacting arched member; and
an external element extending from the first body member to the second body member;
wherein the external element has an undulating planar geometry in which the external element undulates in a single plane;
wherein the external element forms a first peripheral bone contacting element extending from the first body member to the second body member on a first lateral side of the implant; and
wherein the at least one bone contacting arched member extends between the first body member and the second body member independently from the first external element.

13. The implant according to claim 12, wherein the first external element having an undulating planar geometry has a circular cross-sectional shape.

14. The implant according to claim 12, wherein the first external element having an undulating planar geometry has a substantially rectangular cross-sectional shape.

15. The implant according to claim 12, wherein the bone contacting arched member is a superior bone contacting element.

16. The implant according to claim 12, wherein the first body member is located on an anterior side of the implant, and wherein the second body member is located on a posterior side of the implant.

17. The implant according to claim 12, wherein the implant includes a second external element extending from the first body member to the second body member; and
wherein the second external element is disposed on an opposite side of the implant from the first external element.

18. The implant according to claim 17, further including a central bone contacting element extending from the first external element to the second external element.

19. The implant according to claim 18, wherein the bone contacting arched member is attached to the central bone contacting element.

20. The implant according to claim 12, wherein the bone contacting arched member is formed by a bone contacting element including a plurality of arched members;
wherein the plurality of arched members includes at least two arched members extending substantially parallel to and offset with respect to one another.

* * * * *